(12) United States Patent
Jafri et al.

(10) Patent No.: US 11,645,899 B2
(45) Date of Patent: May 9, 2023

(54) RESPONDER NETWORK

(71) Applicant: Avive Solutions, Inc., San Francisco, CA (US)

(72) Inventors: Sameer Jafri, San Diego, CA (US); Micah R. Bongberg, Kirkland, WA (US); Rory M. Beyer, San Mateo, CA (US); Gordon Moseley P. Andrews, Ross, CA (US)

(73) Assignee: Avive Solutions, Inc., Brisbane, CA (US)

( * ) Notice: Subject to any disclaimer, the term of this patent is extended or adjusted under 35 U.S.C. 154(b) by 0 days.

(21) Appl. No.: 17/471,572

(22) Filed: Sep. 10, 2021

(65) Prior Publication Data

US 2021/0407273 A1 Dec. 30, 2021

Related U.S. Application Data

(63) Continuation-in-part of application No. 16/863,068, filed on Apr. 30, 2020, now Pat. No. 11,138,855,
(Continued)

(51) Int. Cl.
| | | |
|---|---|---|
| G08B 21/02 | (2006.01) |
| H04W 4/90 | (2018.01) |
| G08B 25/14 | (2006.01) |
| G08B 27/00 | (2006.01) |
| G08B 25/00 | (2006.01) |
| H04W 4/16 | (2009.01) |
| H04W 4/02 | (2018.01) |
| A61N 1/39 | (2006.01) |

(52) U.S. Cl.
CPC .......... *G08B 21/02* (2013.01); *G08B 25/006* (2013.01); *G08B 25/14* (2013.01); *G08B 27/001* (2013.01); *H04W 4/16* (2013.01); *H04W 4/90* (2018.02); *A61N 1/3904* (2017.08); *H04W 4/02* (2013.01)

(58) Field of Classification Search
CPC ..................................................... G08B 21/02
See application file for complete search history.

(56) References Cited

U.S. PATENT DOCUMENTS

| | | |
|---|---|---|
| 6,292,687 B1 | 9/2001 | Lowell et al. |
| 6,356,785 B1 | 3/2002 | Snyder et al. |
| (Continued) | | |

FOREIGN PATENT DOCUMENTS

| | | |
|---|---|---|
| CN | 105013085 | 11/2015 |
| CN | 108671401 | 10/2018 |
| (Continued) | | |

OTHER PUBLICATIONS

International Search Report and Written Opinion for PCT/US2019/049876, dated Feb. 18, 2020.
(Continued)

*Primary Examiner* — Travis R Hunnings
(74) *Attorney, Agent, or Firm* — Beyer Law Group LLP

(57) ABSTRACT

A variety of methods, medical devices, responder network servers, emergency services interfaces and call center related processes are described that can help improve responder networks designed to get a medical device such as an automated external defibrillator and/or volunteer responders to the scene of a potential medical incident.

24 Claims, 20 Drawing Sheets

Related U.S. Application Data which is a continuation-in-part of application No. 16/741,277, filed on Jan. 13, 2020, now Pat. No. 10,665,078, which is a continuation of application No. 16/562,870, filed on Sep. 6, 2019, now Pat. No. 10,580,280.

(60) Provisional application No. 62/846,346, filed on May 10, 2019, provisional application No. 62/731,306, filed on Sep. 14, 2018.

(56) References Cited

U.S. PATENT DOCUMENTS

| | | |
|---|---|---|
| 6,493,581 B2 | 12/2002 | Russell |
| 6,658,290 B1 | 12/2003 | Lin et al. |
| 6,747,556 B2 | 6/2004 | Medema et al. |
| 6,834,207 B2 | 12/2004 | Miyauchi et al. |
| 6,937,150 B2 | 8/2005 | Medema et al. |
| 6,993,386 B2 | 1/2006 | Lin et al. |
| 7,289,029 B2 | 10/2007 | Medema et al. |
| 8,086,320 B2 | 12/2011 | Saketkhou |
| 8,180,457 B2 | 5/2012 | Matos |
| 8,209,008 B2 | 6/2012 | Hansen et al. |
| 8,565,871 B2 | 10/2013 | Tuysserkani |
| 8,706,225 B2 | 4/2014 | Matos |
| 8,818,522 B2 | 8/2014 | Mass et al. |
| 8,880,168 B2 | 11/2014 | Pearce et al. |
| 8,981,927 B2 | 3/2015 | McSheffrey |
| 9,026,147 B2 | 5/2015 | Galvin et al. |
| 9,035,787 B2 | 5/2015 | Bongberg et al. |
| 9,101,527 B2 | 8/2015 | Madanat |
| 9,232,040 B2 | 1/2016 | Barash et al. |
| 9,289,621 B2 | 3/2016 | Aoyama et al. |
| 9,295,849 B2 | 3/2016 | Elghazzawi et al. |
| 9,307,383 B1 | 4/2016 | Patrick |
| 9,324,120 B2 | 4/2016 | Braun |
| 9,480,852 B2 | 11/2016 | Bonnamy |
| 9,498,152 B2 | 11/2016 | Bowers |
| 9,592,401 B2 | 3/2017 | Freeman et al. |
| 9,619,767 B2 | 4/2017 | Braun |
| 9,628,946 B2 | 4/2017 | Elghazzawi |
| 9,847,030 B2 | 12/2017 | Kadobayashi et al. |
| 9,848,058 B2 | 12/2017 | Johnson et al. |
| 9,872,998 B2 | 1/2018 | Aoyama et al. |
| 9,889,311 B2 | 2/2018 | Horseman et al. |
| 9,897,459 B2 | 2/2018 | Johnson |
| 9,987,193 B2 | 5/2018 | Freeman |
| 10,035,023 B2 | 7/2018 | Das |
| 10,058,469 B2 | 8/2018 | Freeman |
| 10,058,709 B2 | 8/2018 | Tilton, Jr. |
| 10,090,716 B2 | 10/2018 | Stever et al. |
| 10,092,767 B1 | 10/2018 | Newton et al. |
| 10,099,061 B2 | 10/2018 | Buchanan |
| 10,159,848 B2 | 12/2018 | Amann et al. |
| 10,178,534 B2 | 1/2019 | Barash et al. |
| 10,298,072 B2 | 5/2019 | Stever et al. |
| 10,381,118 B2 | 8/2019 | Kellum |
| 10,449,380 B2 | 10/2019 | Andrews |
| 10,504,622 B2 | 12/2019 | Gallopyn et al. |
| 10,543,379 B2 | 1/2020 | Kingston et al. |
| 10,565,845 B1 * | 2/2020 | Beyer ............... G08B 25/005 |
| 10,580,280 B1 | 3/2020 | Picco et al. |
| 10,621,846 B1 | 4/2020 | Beyer et al. |
| 10,638,929 B2 | 5/2020 | Kaib et al. |
| 10,657,796 B2 | 5/2020 | Bowers |
| 10,665,078 B1 | 5/2020 | Picco et al. |
| 10,744,063 B2 | 8/2020 | Freeman |
| 10,792,506 B2 | 10/2020 | Elghazzawi |
| 10,796,396 B2 | 10/2020 | Braun et al. |
| 10,806,939 B1 | 10/2020 | Malott et al. |
| 10,857,371 B2 | 12/2020 | Gustavson et al. |
| 10,861,310 B2 | 12/2020 | Picco et al. |
| 10,946,209 B2 | 3/2021 | Andrews et al. |
| 10,957,178 B2 | 3/2021 | Beyer et al. |
| 2003/0149759 A1 | 8/2003 | Hetherington et al. |
| 2004/0015191 A1 | 1/2004 | Otman et al. |
| 2004/0049233 A1 | 3/2004 | Edwards |
| 2004/0064342 A1 | 4/2004 | Browne et al. |
| 2006/0030891 A1 | 2/2006 | Saltzstein et al. |
| 2006/0041278 A1 | 2/2006 | Cohen et al. |
| 2006/0149321 A1 | 7/2006 | Merry et al. |
| 2006/0149322 A1 | 7/2006 | Merry et al. |
| 2006/0149323 A1 | 7/2006 | Merry et al. |
| 2007/0032830 A1 | 2/2007 | Bowers |
| 2007/0136099 A1 | 6/2007 | Neligh et al. |
| 2007/0162075 A1 | 7/2007 | O'hara |
| 2007/0270909 A1 | 11/2007 | Saketkhou |
| 2007/0299473 A1 * | 12/2007 | Matos ............... A61N 1/3904 607/9 |
| 2008/0250166 A1 | 10/2008 | Edwards |
| 2009/0070148 A1 | 3/2009 | Skocic |
| 2009/0149894 A1 | 6/2009 | Merry et al. |
| 2009/0284348 A1 * | 11/2009 | Pfeffer ............... G08B 25/016 340/7.3 |
| 2009/0284378 A1 * | 11/2009 | Ferren ............... G08B 21/06 340/573.1 |
| 2010/0017471 A1 | 1/2010 | Brown et al. |
| 2010/0286490 A1 * | 11/2010 | Koverzin ............ G10L 17/26 704/231 |
| 2011/0060378 A1 | 3/2011 | Tuysserkani |
| 2011/0071880 A1 * | 3/2011 | Spector ............... H04W 76/50 340/539.13 |
| 2011/0117878 A1 | 5/2011 | Barash et al. |
| 2011/0152702 A1 * | 6/2011 | Goto ............... G16H 40/67 340/7.58 |
| 2012/0232355 A1 | 9/2012 | Freeman |
| 2012/0271370 A1 | 10/2012 | Hochhalter et al. |
| 2013/0012151 A1 | 1/2013 | Hankins |
| 2013/0065628 A1 | 3/2013 | Pfeffer |
| 2013/0296719 A1 | 11/2013 | Packer et al. |
| 2014/0002241 A1 | 1/2014 | Elghazzawi |
| 2014/0004814 A1 | 1/2014 | Elghazzawi |
| 2014/0031884 A1 | 1/2014 | Elghazzawi |
| 2014/0222096 A1 | 8/2014 | Hu et al. |
| 2014/0222466 A1 | 8/2014 | Kellum |
| 2015/0206408 A1 * | 7/2015 | LaLonde ............ A61B 5/349 340/539.12 |
| 2015/0343229 A1 * | 12/2015 | Peterson ............ G16Z 99/00 607/6 |
| 2016/0066653 A1 | 3/2016 | Piva et al. |
| 2016/0133160 A1 | 5/2016 | Packer et al. |
| 2016/0140834 A1 * | 5/2016 | Tran ............... A61B 5/681 340/539.11 |
| 2016/0148495 A1 | 5/2016 | Buchanan |
| 2016/0210581 A1 | 7/2016 | Braun |
| 2016/0213942 A1 | 7/2016 | Elghazzawi et al. |
| 2016/0217691 A1 * | 7/2016 | Kadobayashi ......... G16H 40/20 |
| 2016/0328950 A1 | 11/2016 | Pelletier et al. |
| 2017/0028211 A1 | 2/2017 | Tilton, Jr. |
| 2017/0172424 A1 | 6/2017 | Eggers et al. |
| 2017/0251347 A1 | 8/2017 | Mehta et al. |
| 2017/0281016 A1 | 10/2017 | Elghazzawi |
| 2017/0281461 A1 | 10/2017 | Kokubo et al. |
| 2017/0289350 A1 | 10/2017 | Philbin |
| 2017/0367927 A1 | 12/2017 | Cervantes |
| 2018/0169426 A1 | 6/2018 | Montague et al. |
| 2018/0369598 A1 | 12/2018 | Newton et al. |
| 2019/0038133 A1 | 2/2019 | Tran |
| 2019/0044362 A1 | 2/2019 | Beyer et al. |
| 2019/0099608 A1 | 4/2019 | Elghazzawi et al. |
| 2019/0117983 A1 | 4/2019 | Andrews et al. |
| 2019/0117984 A1 | 4/2019 | Andrews et al. |
| 2019/0117987 A1 | 4/2019 | Beyer et al. |
| 2019/0117988 A1 | 4/2019 | Beyer et al. |
| 2019/0159009 A1 | 5/2019 | Barash et al. |
| 2019/0168010 A1 | 6/2019 | Elghazzawi |
| 2019/0174289 A1 | 6/2019 | Martin et al. |
| 2019/0279327 A1 | 9/2019 | Braun et al. |
| 2019/0306664 A1 | 10/2019 | Mehta et al. |
| 2019/0318827 A1 | 10/2019 | Chiu et al. |
| 2020/0054885 A1 | 2/2020 | Aprile |
| 2020/0090483 A1 | 3/2020 | Picco et al. |
| 2020/0092700 A1 | 3/2020 | Picco et al. |

(56) References Cited

U.S. PATENT DOCUMENTS

| | | | |
|---|---|---|---|
| 2020/0206517 A1 | 7/2020 | Martin et al. | |
| 2020/0221263 A1* | 7/2020 | Sturman | A61N 1/3904 |
| 2020/0242907 A1 | 7/2020 | Beyer et al. | |
| 2020/0286352 A1* | 9/2020 | Beyer | G08B 27/005 |
| 2020/0286353 A1* | 9/2020 | Jafri | G08B 21/02 |
| 2020/0373005 A1 | 11/2020 | Halsne et al. | |
| 2021/0142639 A1* | 5/2021 | Beyer | G08B 25/14 |
| 2021/0228893 A1* | 7/2021 | Akram | A61N 1/3904 |
| 2021/0357456 A1* | 11/2021 | Hale | G01W 1/10 |
| 2022/0092957 A1* | 3/2022 | Beyer | A61N 1/3993 |

FOREIGN PATENT DOCUMENTS

| | | |
|---|---|---|
| CN | 111539866 | 8/2020 |
| DE | 202004002106 | 6/2004 |
| EP | 1157717 | 1/2005 |
| EP | 2218478 | 8/2010 |
| EP | 2879759 | 10/2019 |
| JP | 2001/325689 | 11/2001 |
| JP | 2015-58030 | 3/2015 |
| KR | 20160012239 | 2/2016 |
| KR | 101780214 | 10/2017 |
| KR | 102152282 | 9/2020 |
| WO | 2010/66014 | 6/2010 |
| WO | 2018/069383 | 4/2018 |

OTHER PUBLICATIONS

Beyer et al., U.S. Appl. No. 17/100,154, filed Nov. 19, 2020.
Bongberg et al., U.S. Appl. No. 17/100,313, filed Nov. 19, 2020.
Extended European Search Report dated Feb. 1, 2022 from European Application No. 19860873.9.
Japanese Office Action dated Oct. 18, 2022 from Japanese Application No. 2021-510089.

* cited by examiner

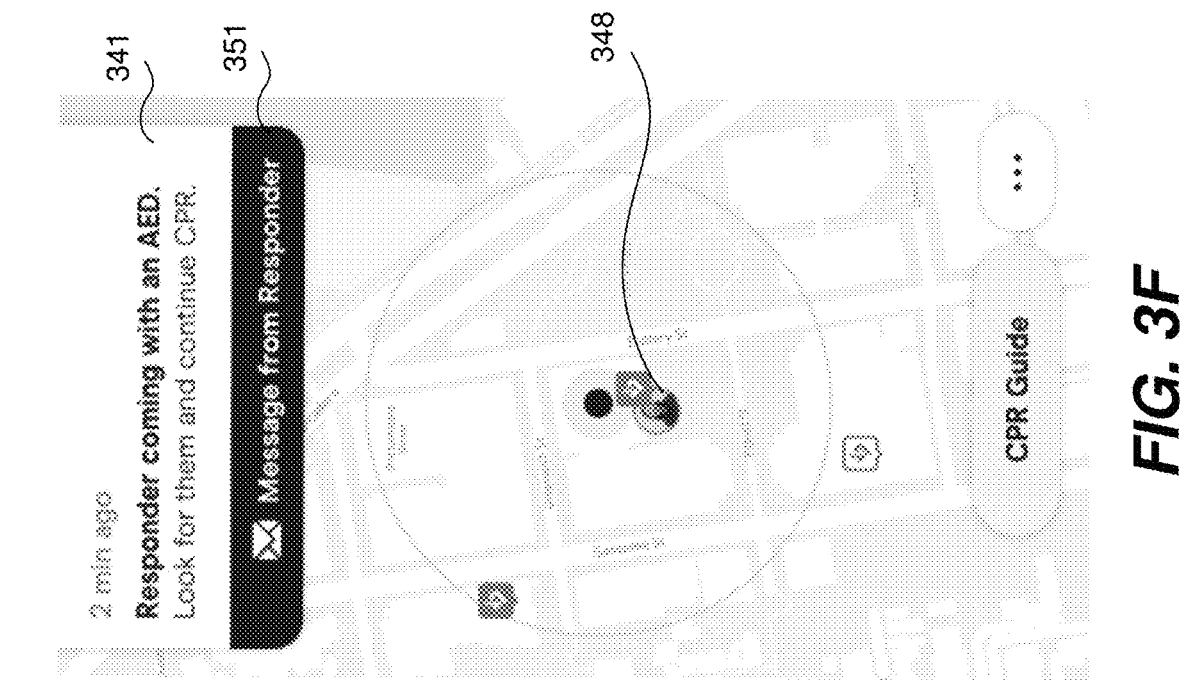

RESPONDER NETWORK

CROSS-REFERENCE TO RELATED APPLICATIONS

This application is a Continuation-in-Part of U.S. application Ser. No. 16/863,068, filed on Apr. 30, 2020, which is a Continuation-in-Part of U.S. application Ser. No. 16/741,277, filed on Jan. 13, 2020 (now U.S. Pat. No. 10,665,078, issued on May 26, 2020), which is a Continuation of U.S. application Ser. No. 16/562,870, filed on Sep. 6, 2019 (now U.S. Pat. No. 10,580,280, issued Mar. 3, 2020), which claims the priority of U.S. Provisional Patent Application Nos. 62/731,306 filed Sep. 14, 2018, and 62/846,346 filed May 10, 2019, all of which are incorporated herein by reference in their entirety.

FIELD

The present invention relates generally to the creation and implementation of a public responder network—as for example, a network of responders willing to respond to cardiac arrest incidents that may happen nearby. A variety of methods, devices and software applications suitable for supporting and utilizing such a network in the event of an emergency incident are described.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed such that they can be used by a lay person in situations where professional medical personnel are not available.

Given their potential to save lives, automated external defibrillators have been deployed in a relatively wide variety of public and private locations so that they are available in the event that a person in the vicinity goes in to cardiac arrest. By way of example, AEDs may be found in corporate and government offices, shopping centers, airports, airplanes, restaurants, casinos, hotels, sports stadiums, schools, fitness centers and a variety of other locations where people may congregate.

Although the availability of AEDs has increased over the years, their relatively high cost tends to limit their placement and many locations including schools, sports fields, and a plethora of other places where people congregate don't have an on-site AED available. Thus there are many times, locations and events where no AED is available when a cardiac arrest incident occurs. Even when an AED is nearby when a sudden cardiac arrest incident occurs, the AED is often not used because either its presence is unknown or the device seems intimidating to bystanders who are reluctant to try to use a device that they are unfamiliar with in an emergency setting.

A number of efforts have been made to increase the public awareness of public access defibrillators. By way of example, there are a number of websites and downloadable apps that show the location of registered or otherwise known public access defibrillators. A few representative solutions include Pulsepoint (www.pulsepoint.org); AEDMAP (www.aedmap.org) and HeartSafe (www.heartsafe.org.uk). Although such efforts can be very helpful, to be used at the time of a cardiac incident, they require a bystander to lookup the location of nearby AED and go fetch the nearest AED which hopefully is present at its marked location and in good working order.

Another effort is Pulse Point Respond (www.pulsepoint.org/pulsepoint-respond/), which is a community based program in which volunteer citizen responders who are trained in CPR and AED use, are informed of nearby cardiac incidents that are occurring in public places. The concept behind the citizen responder projects is that a citizen responder may be able to reach a cardiac incident faster than conventional emergency medical services. This is particularly critical for cardiac arrest incidents where statistics show that survival rates decrease at a rate of on the order of 10% with each passing minute. The Pulse Point Respond system is tied in with emergency services so that the call for citizen responders is triggered by emergency services.

Although these types of systems are clearly beneficial, there are continuing efforts to develop additional and improved techniques that can further increase public awareness, help shorten cardiac arrest response times and/or otherwise improve cardiac arrest survival rates.

SUMMARY

To achieve the foregoing and other objects a variety of methods, medical devices, servers, interfaces and call center related processes are described that can help improve responder networks.

In one aspect a response network server identifies a set of medical devices to be queried in response to receiving a request for assistance. The request for assistance indicates the location of a potential medical incident. Status queries are sent to the identified medical devices to verify their current location and operational status. After receiving at least one status query response an incident alert message is sent to selected responding medical devices and/or selected volunteer responder requesting assistance at the scene of the incident. In some embodiments the medical devices are defibrillators and the request for assistance is a request for defibrillator assistance.

The selection of which devices to send incident alerts messages to can be based on a variety of factors including the device's distance or travel time from the incident, the device's reported status, past incident response history, and/or a variety of other factors.

In some embodiments, the re request for assistance is received directly or indirectly from an emergency call center. In some circumstances the request for assistance is received indirectly from an emergency call center through an emergency services interface that is configured to communicate with a multiplicity of different emergency call centers and to transmit emergency incident data from other devices to the multiplicity of different emergency call centers. In other embodiments, the request for assistance is received directly or indirectly from an app on a mobile computing device that is at the scene of the potential medical incident.

Communications with any particular emergency response device (e.g. defibrillator, emergency kit or other medical device) are sent to a communication unit associated with the device. The communication unit may be an integral part of the medical device or part of an independent interface unit. In various embodiments, the interface unit may be physically attached to the medical device or separate from, but relatively close to the medical device. In other embodiments, the interface unit may be part of a base station (e.g. cabinet, stand, etc.) that the medical device is stored in.

In the context of defibrillators, in some embodiments, status queries are sent to a relatively large number of defibrillators whereas the nearby incident alert messages may be sent to a selected subset of the defibrillators that received a status query. In some embodiments, the selected subset only includes defibrillators from which a status query responses were received. A variety of different selection and/or filtering rules can be used to identify the subset of defibrillators to actually be notified of an incident. In various embodiments, selection of defibrillators to receive an incident nearby message may be based at least in part on factors such as: whether the defibrillator responded to a status query; the current location and/or current status reported by the defibrillator; an estimated distance or travel time to the incident; a prior incident response history associated with such defibrillator; and/or a variety of other factors. Similar factors may be used in identifying volunteer responders to send volunteer incident alerts to.

In some embodiments, the responder network server maintains a database that includes the current location and current functional status of defibrillators in its network.

In another aspect a defibrillator system is arranged to send a current status message in response to receiving an electronic status query. When a nearby incident message is received, the system generates a nearby incident alert that indicates that there is a cardiac emergency nearby for which the defibrillator may be useful.

In various embodiments, the nearby incident alert includes an audio alert, a visual alert message or a combination of both. Visual alert messages may be displayed on a display screen on the defibrillator itself, or an interface device associated with the defibrillator.

In some embodiments, the visual alert message includes an indication that there is a nearby emergency that can use a defibrillator and a GUI widget that can be selected by a user to indicate the user's willingness to help. Selection of the GUI widget causes an incident accepted message to be sent to a responder network server. In some embodiments, a map is displayed to show the incident's location. In other embodiments a user may indicate their willingness to help via a spoken command or other suitable means.

In some embodiments, a defibrillator receiving a status query responds by opening a connection with the responder network server over a different channel than the status query was received on. A status report is then sent to the network server via the new connection. In some embodiments, entirely different communications protocols are used in the different channels. For example, a messaging technology such as SMS messages may be used for the status query whereas an IP communications protocol or other suitable protocol may be used in for the second channel.

In some embodiments, the defibrillator system is a portable modular defibrillator system that includes a base defibrillator unit and a detachable interface unit that is mounted on and detachably attached to the base defibrillator unit. In some implementations, the interface unit includes the communication unit and display screen.

In another aspect an emergency services interface is used to facilitate communications between various call centers and a responder network server. The emergency services interface is configured to communicate with a multiplicity of different emergency call centers. It is also configured to receive real-time incident data from connected devices and communicate the real-time incident data directly to appropriate ones of the emergency call centers. In some embodiments, a request for volunteer assistance generated by an emergency call center is sent to the emergency services interface. The emergency services interface, in turn, sends a request for assistance to a responder network server. The request for assistance includes the location of the potential medical incident.

In another aspect defibrillator incident data may be transmitted from a defibrillator to selected medical personnel and/or facilities via a series of intermediaries including a medical device network server, an emergency services interface and a call center.

In various embodiments the defibrillator incident data may include one or more of: an indication of a number of shocks delivered to a patient; information about the nature or timing of each such shock; one or more ECG segments; cardiac rhythm classifications made by the defibrillator's classifier and/or any other available information that may be useful to medical personnel.

In yet another aspect, methods are described for automatically analyzing incident records received from a call center to determine whether an automated external defibrillator may be useful to an incident referenced by the incident record. When it is determined that an AED may be useful to an incident, an incident alert is automatically electronically transmitted to one or more registered volunteer responders, and/or one or more automated external defibrillators to encourage responders to go to the scene of the incident.

In another aspect, a call center computer aided dispatch unit having graphical user interface widget suitable for selection by a call center operator is described. Selection of the graphical user interface widget causes the computer aided dispatch unit to transmit a request for automated external defibrillator assistance. The request for automated external defibrillator assistance including an indication of a location of a potential cardiac arrest incident for which assistance is desired. The request for automated external defibrillator assistance is a general request that does not identify any specific responder or defibrillator to be notified of the potential cardiac arrest incident. The request for automated external defibrillator assistance is sent to a responder network that identifies at least one of (a) a set of defibrillators, and (b) a set of volunteer responders, to notify of the potential cardiac arrest incident.

In another aspect AEDs are configured to direct volunteer responders to the scene of a nearby cardiac arrest incident. In some such embodiments, an AED system is configured to generate a nearby incident alert in response to reception of an incident message. The AED system is also configured to receive a responder's acceptance of the incident indicating a willingness to help by bringing the AED to the location of the potential cardiac arrest incident, and convey an indication of the responder's acceptance of the incident to a remotely located server. Additionally, the AED system provides a map showing the location of the potential cardiac arrest incident and/or directions to the location of the potential cardiac arrest incident, such that the responder can utilize the map or directions to navigate to the location of the potential cardiac arrest incident.

In some embodiments, an accept incident GUI element is provided in conjunction with the nearby incident alert that the responder may select in order to indicate that the responder is willing to take the AED to the location of the potential cardiac arrest incident.

In some embodiments, the current location of the AED is shown on the map and the current location displayed on the map is updated as the responder navigates to the location of the potential cardiac arrest incident.

In some embodiments, the user interface is configured to automatically transition to displaying at least one of (i) and arrived message; or (ii) an AED operating instruction, when the AED is determined to have arrived at the location of the potential cardiac arrest incident.

In another aspect the AED system is configured to display a map on that shows a current location of the AED and the location of the potential cardiac arrest incident, whereby a responder carrying the AED may utilize the map displayed on the display screen to navigate to the location of the potential cardiac arrest incident. The current location of the AED is periodically updated on the map as the responder navigates with the AED towards the location of the potential cardiac arrest incident.

In some embodiments, the AED system is configured to support messaging between the responder and a witness present at the location of the potential cardiac arrest incident.

BRIEF DESCRIPTION OF THE DRAWINGS

The invention and the advantages thereof, may best be understood by reference to the following description taken in conjunction with the accompanying drawings in which:

FIGS. 3A-3G are a sequence of cards illustrating a representative app flow and user interface that facilitates requesting help from nearby public responders from the scene of a potential cardiac arrest incident using an app that can connect to a public responder network.

In the drawings, like reference numerals are sometimes used to designate like structural elements. It should also be appreciated that the depictions in the figures are diagrammatic and not to scale.

DETAILED DESCRIPTION OF THE PREFERRED EMBODIMENTS

The present invention relates generally to the creation and implementation of a public responder network—as for example, a network of defibrillators (e.g. AEDs) available for use during a potential cardiac arrest incident and volunteer responders willing to respond such an event. A variety of methods, devices and software applications suitable for supporting and utilizing such a network in the event of an emergency incident are described. The inventions are described primarily in the context of a network of defibrillators and volunteers willing to respond to cardiac arrest incidents. However, it should be appreciated that a similar approaches and systems can be used in conjunction with responder networks involving other types of medical incidents, treatments and/or devices.

The Applicant is developing automated external defibrillator systems that include a number of connectivity features and/or are well suited for use in conjunction with mobile phones. By way of example, U.S. Pat. No. 10,029,109 and U.S. patent application Ser. No. 16/145,657 (each of which is incorporated herein by reference) describe a few such devices.

Figure 1A:
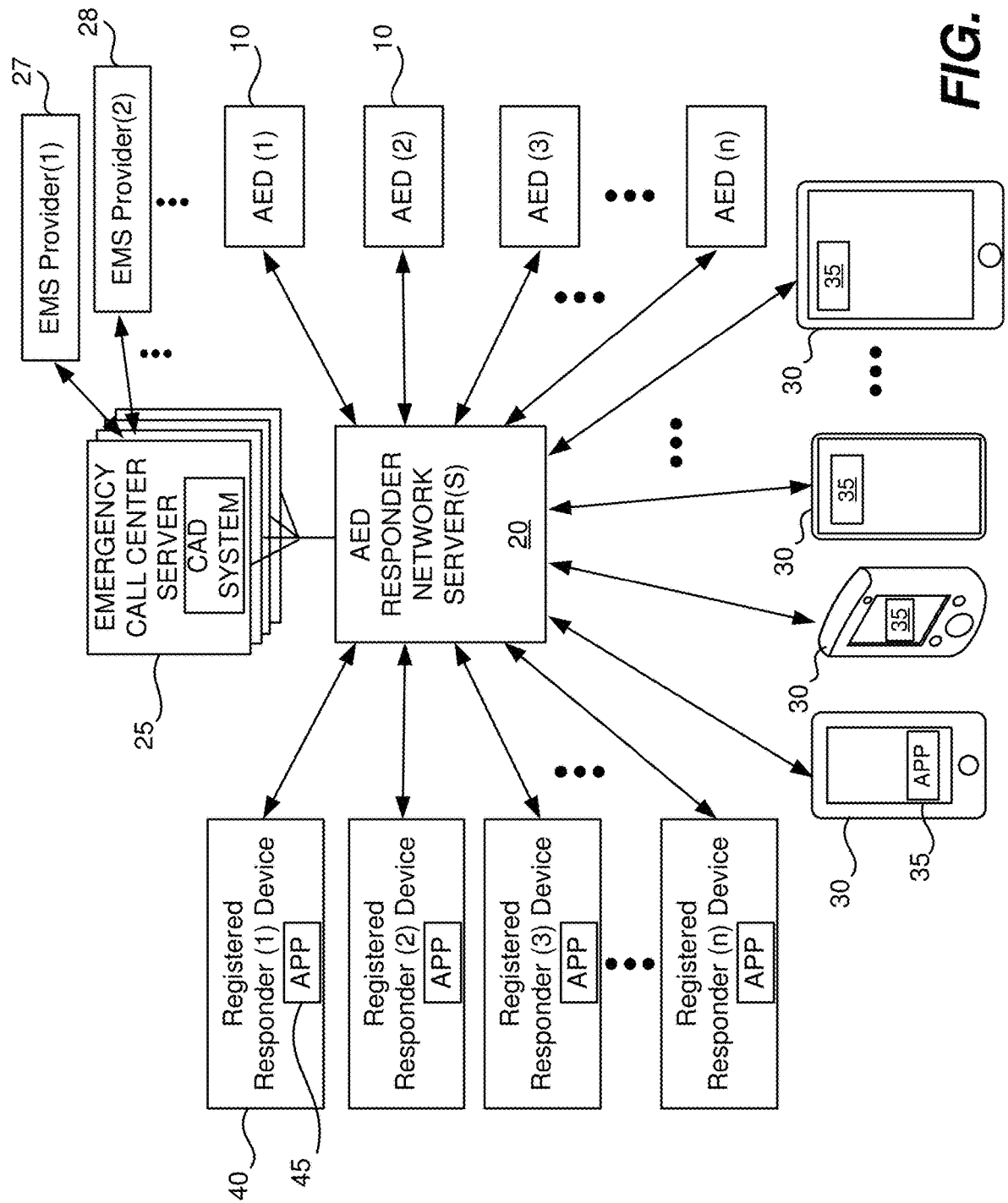
FIG. 1A is a schematic diagram illustrating components of a public responder network for notifying potential responders of nearby potential cardiac arrest incidents.
Figure 1B:
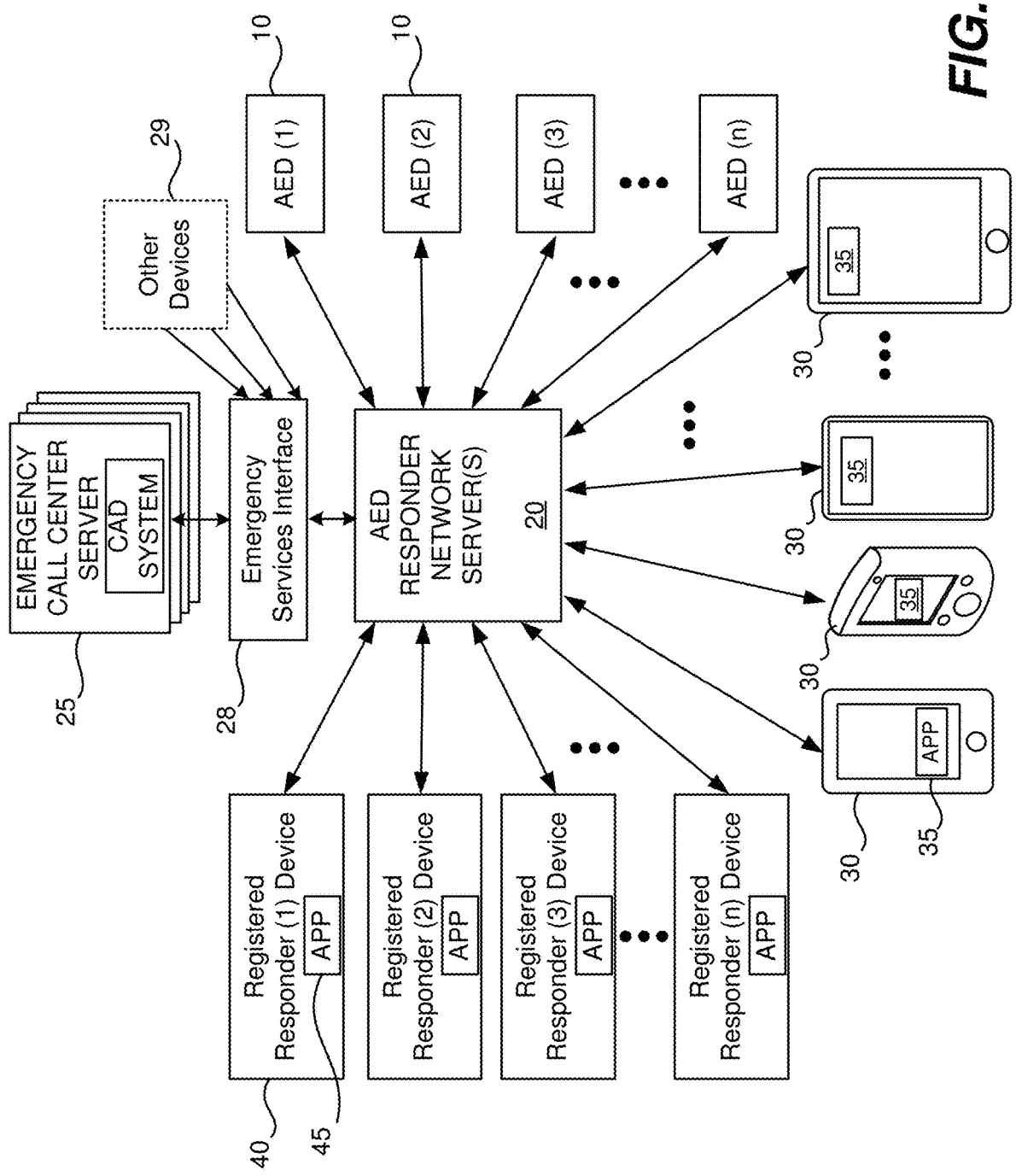
FIG. 1B is a schematic diagram illustrating components of an alternative public responder network for notifying potential responders of nearby potential cardiac arrest incidents that utilizes an emergency services interface.

Components of a responder network of the type contemplated herein are diagrammatically illustrated in FIGS. 1A and 1B. In the embodiment illustrated in FIG. 1A, the network includes a number of AEDs 10 that have connectivity features which facilitate communications with one or more servers—which is/are referred to in FIG. 1A as AED response network server(s) 20. Some of the AEDs described in the incorporated patents and patent application work well for this purpose, but the network is not in any way limited to such AED. In some embodiments, some of the AEDs 10 may be modular defibrillator systems that include a fully functional base defibrillator and an interface unit that is mounted on and detachably attached to the base defibrillator unit to provide a unitary portable modular defibrillator. In such embodiments, the interface unit may include components such as a display screen and a communication unit suitable for communicating with the AED response network server through an appropriate communications network. The incorporated U.S. patent application Ser. No. 16/145,657 describes some such systems. In other embodiments, the communications capabilities may be provided in a variety of different ways. For example, the communications module may be incorporated into a unitary defibrillator housing, or in a modular system, into the base defibrillator unit. Alternatively, the communications unit may be a unit that plugs into a defibrillator or any take any other suitable form.

The AED response network server(s) 20 may be arranged to communicate directly or indirectly with existing emergency response networks and systems, including, for example, computer aided dispatch (CAD) systems commonly used by emergency call/dispatch centers. These are sometimes collectively referred to as emergency services servers (25) and a particular class of emergency services servers referred to as emergency call center servers(s) is illustrated in FIG. 1A. Emergency call centers are centers such a Public Safety Answering Points (PSAP) Center, 911 call centers in the U.S. and Canada, 112 call centers in Europe, 999 call centers in some jurisdictions and other such emergency services call centers.

The emergency call/dispatch centers 25 are typically able to communication separately with a variety of emergency medical service providers (EMS providers) 27 which may include emergency medical technicians, ambulance services, fire department personnel, etc.

In various embodiments, the AED response network server can be hosted by an advocacy group or a private party such as a defibrillator manufacturer or an entity that manages a large number of AEDs. Alternatively, the functionality of AED response network server(s) 20 could be incorporated into a server (or servers) within an emergency services interface (discussed below). In other embodiments, the functionality of the AED response server(s) 20 can be incorporated into other components of public safety and/or emergency response networks.

The network also includes a number of user devices 30 having a user app 35 or other suitable software installed thereon that is also configured to communicate with one or more of the AEDs, and with the AED response network server 20. The AED user devices 30 are frequently (but not necessarily) devices associated with the AED's owners, administrators and/or other responsible parties. The AED user devices 30 may take any of a wide variety of different forms including mobile phones, tablet computers, as well as other types of personal communication and/or computing devices. The network also has a number of registered volunteer responders who have registered to indicate their desire to receive notification of nearby emergency incidents for which assistance may be helpful. In the context of a responder network focused on sudden cardiac arrest, the responders would presumably and preferably be trained in CPR and the use of an AED.

The volunteer responders have their own user devices 40 (e.g. smart phones, tablets, smart watches or other computing or mobile/personal communication devices) which have a responder app 45 or other suitable software installed thereon with which they can communicate and receive communications from the AED response network server 20. Like the user devices 30 and user app 35, the responder user devices 40 and responder app 45 may take a wide variety of different forms (e.g. smart phones, tablets, or other computing or mobile/personal communication devices) and they are labeled differently in the drawings merely to highlight the different context that the devices and app are used for. In some embodiments, a single app may be used as both apps 35 and 45 with the primary difference being whether the user has registered as a volunteer responder and the functionality of the app that may be accessed after such registration. Of course, in other embodiments separate apps may be provided. It should be appreciated that there is no need for all of the apps to be the same and/or to come from one source. Rather, the emergency response functionality can be incorporated into a wide variety of different applications or software components provided by different entities, including different defibrillator manufacturers, different health service providers, different advocacy groups, different emergency service providers, different user device manufacturers, etc.

In some specific implementations, the user app may be embodied in the form of an AED app that is designed to be capable of use in conjunction with selected defibrillators during the event of an emergency to help guide a lay responder through the use of the AED and/or to help facilitate the transmission of incident information to emergency responders and other concerned medical personnel. Thus, for convenience, in much of the discussion below, the app is referred to as an AED app. However, it should be appreciated that the user application software may take a very wide variety of forms and is not intended to be limited to apps having AED support functionalities.

The AED response network server(s) 20 can also take a wide variety of different forms and are generally intended to refer to any central systems or combinations of systems configured to execute the necessary functionality of the server. By way of example the AED response network server may take the form of one or more computing devices, server clusters, distributed computing nodes on a network or the combined forces of multiple distinct systems. Such servers can be operated by public or private entities of any nature including emergency services, non-profit advocacy organizations, healthcare organizations, medical device companies, government agencies and/or any other suitable entities. The AED response network servers can be dedicated to handling AED response network actions, they can be integrated into AED management server platforms, they can be integrated into components of existing emergency services servers, and/or they can be deployed as part of a variety of other now existing or later developed systems.

FIG. 1B illustrates another representative responder network architecture. This embodiment is quite similar to the embodiment discussed above with respect to FIG. 1A except that an emergency response network interface or an emergency services interface 28 serves as an interface between the AED response network server 20 and the emergency call centers 25. In the United States, RapidSOS is currently the largest emergency response network interface and is well suited for such applications. One particularly desirable feature of RapidSOS is that they currently have relationships with a large percentage of the emergency call centers in the United States and are already set up to send incident related data received from other connected devices 29 to various call centers—although they do not currently serve as an intermediary between call centers and any defibrillators or defibrillator networks. Although RapidSOS is mentioned specifically, it should be appreciated that the same approach can be used with any or with multiple different intermediaries as appropriate.

Figure 2A:
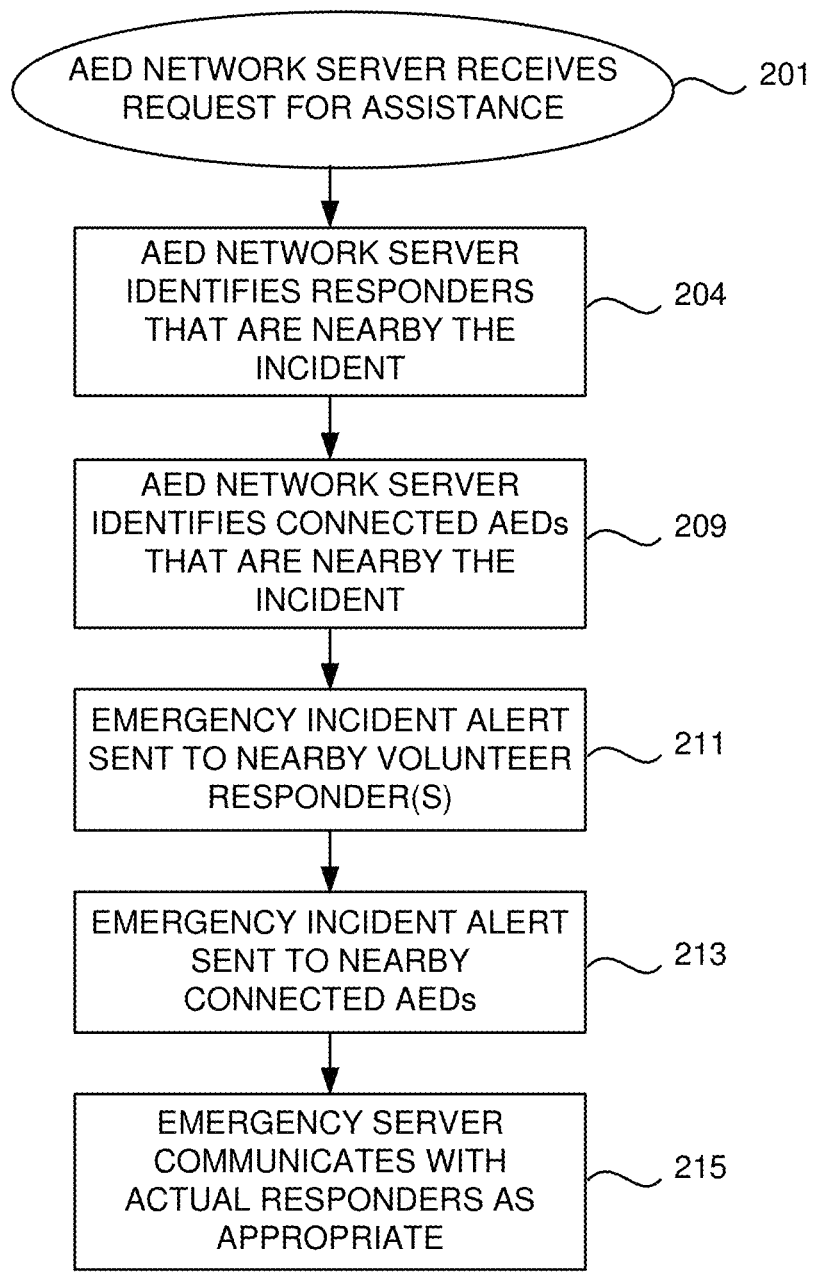
FIG. 2A is a flow chart illustrating a flow suitable for generating an incident alert to nearby volunteer responders and AEDs in response to a request for public AED assistance.

When a cardiac arrest incident occurs, the AED response network server 20 may receive a request for assistance from public responders. The request for assistance can come from a variety of different sources, including from an emergency services server 25 (directly or indirectly through an emergency services interface), a user app 35 or from any other suitable system including other emergency personnel dispatch systems such as police or fire dispatch systems. FIG. 2A is a flow chart illustrating a flow suitable for generating an alert to nearby public AEDs and public responders in the event of a potential cardiac arrest incident in accordance with one embodiment.

When a request for assistance is received (step 201), the AED response network server 20 attempts to identify and select one or more registered volunteer responders and/or volunteer responder devices that are nearby the incident (step 204). The AED response network server also attempts to identify and select one or more known connected AEDs that are nearby the incident (step 209). The protocols, processes and algorithms used to identify suitable volunteers responder, volunteer responder devices and AEDs may vary widely and a few suitable approaches are given as examples below.

The AED response network server then sends an emergency incident nearby alert to the selected registered volunteer responder(s) that are close to the incident (step 211). The alert may be sent via any of a variety of different messaging technologies, including Apple IOS and Android push notification services, SMS text messages, other text or voice messaging protocols, multimedia messaging protocols (e.g., MMS), instant messaging or iMessage technologies, e-mail, etc. If a volunteer responder is nearby that either (a) has an AED or (b) can readily access an AED, then they can grab an AED and quickly bring the AED to the scene of the incident. In many situations, such a volunteer responder who may have an AED, or may know the location of a nearby AED, may be able to bring an AED to the scene quicker than a bystander to the incident trying to locate and fetch an AED or the time that it takes EMS to arrive. The emergency incident nearby alert may be sent to any device(s) associated with the volunteer responder(s) that have been designated to receive such messages. Often this will be a Smartphone or similar mobile communication device. However messages may be sent to any of a number of other types of devices in addition to, or in place of, a Smartphone, as for example, a tablet computer, a PDA, a smart watch, a smart speaker, a virtual assistant, a security system (e.g., a home, office, neighborhood or community security system), etc.

It should be appreciated that volunteer responder devices are not limited to devices associated with a specific individual. For example, the security guard station of a hotel, business, country club or living community may have a connected device that is registered to receive incident notification pertinent to their establishment or community. In another example, a home security network may be registered to receive incident notifications. Of course, there are many other examples as well.

In parallel with the notification of any nearby volunteer responders, emergency alert notifications may also be sent directly to any connected AEDs 10 that are close to the incident (step 213). As will be explained in more detail below, the notified AED can issue an emergency nearby alert signal meant to attract the attention of personnel or bystanders nearby the AED of the incident and request that they bring the AED to the incident location. Typically, such messages would only be sent to connected AEDs that have opted into the AED responder network.

In some embodiments, at least some of the AEDs 10 can be queried to report their current functionality status and current location. When such capabilities, exist, each of the AEDs that are believed to be nearby the incident can be queried (pinged) to provide its current status/location as part of AED identification step 209. Each of pinged AEDs then responds giving its current status and location information and that current information can be used to help determine which AEDs to send an emergency incident alert to in step 213.

After emergency nearby alerts have been sent to any nearby registered volunteer responders and/or registered connected AEDs, the AED response network server can communicate with any responder(s) that agree to respond to the incident as appropriate to help guide them to the location of the incident and convey other information that may be helpful in responding to the incident (step 215).

It should be appreciated that there are a number of scenarios where causing the AED to issue an emergency nearby alert may result in a defibrillator and possibly even a trained responder arriving at the site of a cardiac arrest incident faster than would otherwise occur. For example, in many circumstances a defibrillator may be positioned at a location that is near a designated responder—as for example, in the context of a school setting, the defibrillator may be positioned near (or in) the office of a coach, administrator, nurse or teacher that is a trained responder. In the context of an office building, the defibrillator may be positioned near an administrator or other employee that is a trained responder. When the AED issues an alert, the alert may be heard by the trained responder. In such circumstances there is significant value to notifying the potential responder(s) of an emergency incident that may require a defibrillator in real time so that they can go to the scene and provide assistance as needed. Even when a designated responder (or registered volunteer responders) is not immediately available, there may be other responsible personnel near the location of a defibrillator and the alert generated by the AED will notify such personnel of the occurrence of a cardiac event in their vicinity that they may be able to help respond to. Again using the context of a school setting, other administrators, teachers, coaches or other responsible personnel that happen to be near the defibrillator at the time an incident can be encouraged to quickly take the defibrillator to the location of the incident. Still further, there is even value to informing bystanders (e.g. fans at a sporting event, students or visitor in the school, bystanders in a public space, etc.) that a defibrillator is needed at a nearby emergency incident since it is possible that such a bystander may be motivated to take the AED to the location of the emergency. Although the examples above focus somewhat on the context of a school, it should be appreciated that the same motivations apply in a wide variety of different scenarios.

As previously discussed, when the AED response network server 20 receives a request for volunteer responders (e.g., step 201 of FIG. 2A) or otherwise determines that a volunteer responder may be useful in a particular situation, the server will try to identify nearby volunteer responders and/or nearby AEDs that may be useful for volunteer responders. (e.g., steps 204 and 209 of FIG. 2A). There are a wide variety of selection protocols that may be used to identify potential responders and AEDs.

As discussed above, some connected AEDs have the ability to report their current status and current location. The location can be identified based on any of a wide variety of location services that may be available to pinpoint the location of the AED including: Global Positioning System (GPS) (or more broadly GNSS) chips within the AED or an interface unit attached to the AED or a cabinet associated with AED; cellular or Wi-Fi locating technologies; metropolitan beacon systems; etc. In such embodiments, the AED response network server can ping each of the connected AEDs that are believed to be within a designated distance or response time of the patient. As suggested above, the designated distance may be within a defined radius from the incident, or may be based on more sophisticated measures of distance such as expected path. Alternatively, when available, estimated response times can be used.

The queried AEDs each communicate their functionality status and location to the AED response network server to inform the server as to whether they are in adequate operating condition to be utilized on a patient, otherwise defined as "functional AEDs." Once AED response network server 20 identifies the functional AEDs within a defined distance of the patient, the AED response network server 20 may send an emergency alert (step 213) to any such AEDs deemed appropriate. It is important to note that if any of the AEDs communicate with the AED response network server that they are not in adequate operating condition, otherwise defined as "non-functional AEDs", the server will eliminate these AEDs from consideration and not send these AEDs an emergency alert. The emergency alert that a "functional AED" receives activates an audible and/or visual signal on the identified AEDs signifying that there is an emergency situation for which bystander assistance would be helpful. If a bystander notices the alert, they can "accept" the emergency indicating a willingness to bring the AED to the scene, a map and/or directions is/are displayed on the AED that the responder can use to navigate to the patient's location. Additionally or alternatively, audible directions may be provided to the user.

A variety of different factors can be considered in determining whether to determine which AEDs are notified of a nearby incident. In some embodiments, certain functionality related status characteristics are included. For example a unit with a low battery or expired pads or a unit that is outside of the recommended operating temperature may be assigned a lower priority, but may still be selected for notification if it is otherwise the best or only option.

Somewhat similarly, if a volunteer responder accepts an emergency, a suitable map and/or directions may appear on the volunteer's responder device 40 (e.g., smart phone) and guide the volunteer responder as appropriate. In other circumstances the destination (e.g. a destination address or other identifying information) may be additionally or alternatively provided so that the volunteer responder may enter the destination in their own directions app as desired.) It should be appreciated that there may be several communications back and forth between the AED response network server 20 and the volunteer responder as appropriate. For example, the responder may be asked whether they have immediate access to an AED. If so, a map may be displayed on the responder device to guide the volunteer directly to the incident. If not, the map may display the location(s) of available AEDs and guide the volunteer to a functional AED that is the closest to being on the way to the incident and then to the incident itself so that the volunteer can bring the AED.

When desired, the AED response network server can also intelligently direct volunteer responders in a coordinated manner. For example, if a volunteer that saw an emergency nearby alert on an AED has affirmatively indicated that they are responding to the incident by bringing the AED, a registered volunteer responder who is closer to the incident but doesn't have an AED in hand may be directed to proceed directly to the incident rather than diverting out of their way to find an available public AED. Of course, the specific protocols and priorities utilized in directing multiple volunteer responders can vary widely based on the priorities and design goals of the responder network management. This can include decisions regarding: how many volunteers and/or AEDs to send incident notifications to; when to call off additional potential responder(s) (if ever) in the event that one or more other responders have affirmatively indicated that they are responding to the incident; when to terminate further broadcasts of an incident alert (e.g. due to professional emergency medical personnel arriving on the scene, or due to responses by other); how many AEDs to try to bring to an incident; whether and in what circumstances volunteer responders may be directed to travel directly to an incident even if they don't have an AED in hand; etc.

Figure 2B:
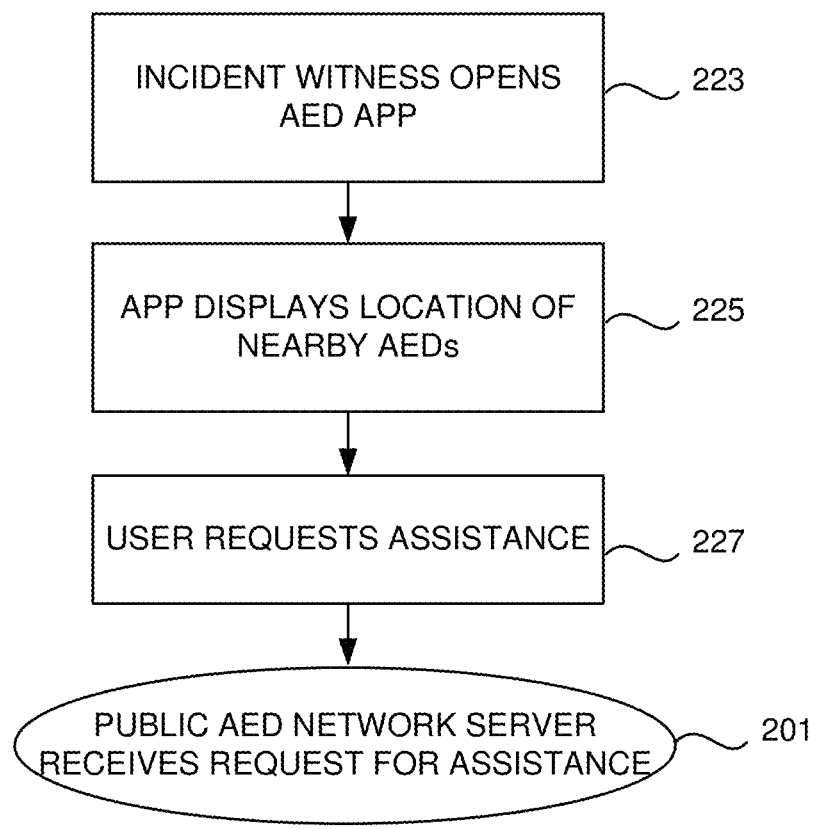
FIG. 2B is a flow chart illustrating a flow suitable for initiating a request for public assistance from the scene of a potential cardiac arrest incident in accordance with one embodiment.
Figure 2C:
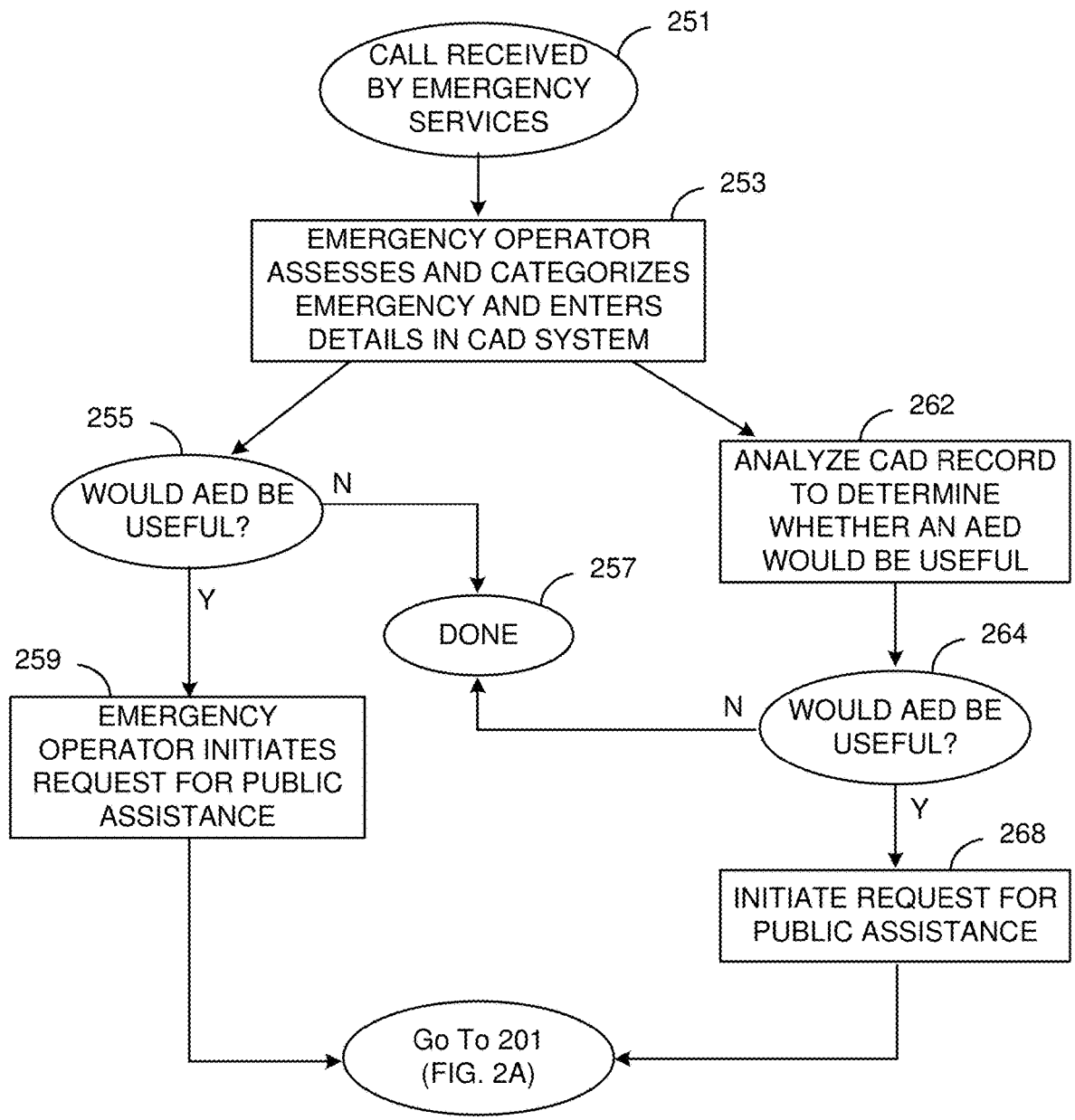
FIG. 2C is a flow chart illustrating a flow suitable for initiating a request for public assistance from a call to emergency operators about a potential cardiac arrest incident in accordance with another embodiment.

There are a number of ways that the initial request for assistance (201) can be triggered. In some circumstances, the request for assistance may be generated by a witness or bystander at the scene who expressly requests assistance through a user app 35 on their phone. FIG. 2B is a flow chart illustrating a representative workflow suitable for generating such a request in accordance with one such embodiment. In other circumstances, the initial request for assistance may come from an emergency call center or be trigger based on information received from such as system. FIG. 2C is a flow chart in accordance with a second embodiment illustrating a representative workflow suitable for generating a request for assistance based on a call made to emergency services (e.g., a 911 call). In still other circumstances the initial request for assistance can come from other sources such as police or fire dispatch centers or any other source that is able to communicate directly or indirectly with the AED network server 20.

In the embodiment illustrated in FIG. 2B, a user at the scene of a potential cardiac incident opens an application that includes volunteer responder assistance request functionality (step 223). As suggested above, such functionality can be incorporated into an AED app 35 or any of a variety of other application programs. Such an app may be executable on a variety of devices including cell phones, tablet computers, defibrillator interface devices, etc.

When the AED app opens, it provides a mechanism for the user to access a variety of features. One such feature is an AED map that shows the location of public access AEDs that are nearby the incident (step 225). In some embodiments, the AED map is included in the initial screen that is shown when the AED app is opened—while in others, a mechanism is provided for the user to readily access the AED map. The AED map can be particularly useful in emergency situations in which the witness to an event does not have immediate access to an AED because the map shows the location of any known or registered public access AEDs that are near the user's location. If extra help is available a bystander can be sent to retrieve the nearest AED.

In addition, if the situation warrants, the user has the ability to request assistance from any nearby volunteer responders by indicating that help, and/or an AED are needed (step 227). Again, this help request is particularly useful in circumstances in which the user doesn't have immediate access to an AED since a volunteer responder that happens to be nearby the incident may have or have access to an AED that can be brought to the scene of the incident more quickly than an AED can be found and returned to the scene by a witness to the event. This can be even more important when the user is alone at the scene of the incident because CPR should typically be performed on the patient and not performing CPR for an extended period while the user searches for an AED can significantly reduce patient survival chances.

The assistance request may be generated by selecting an appropriate GUI button or other appropriate GUI construct which causes a help request message to be transmitted to the AED response network server. The message indicates that help is desired and provides the location of the sending device with as much detail as is available. A particular example of an interface for generating an assistance required request is described below with reference to FIG. 3A et. seq.

The user request for assistance is transmitted to the AED response network server 20 which initiates a request for public volunteer responders as described above with reference to FIG. 2A.

If/when the user indicates that this is an emergency situation, the user or a bystander is preferably encouraged by the app to call emergency services (e.g., 911 in the United States) if that hasn't already been done. This step is important to ensure that emergency medical personnel are dispatched to the incident as soon as possible. Such a call to emergency services may optionally be facilitated by the app although that is not necessary in various embodiments because in many circumstances users or bystanders would be able to independently call emergency services. In still other embodiments, the AED response network server can be configured to automatically forward a notification to the emergency call center that is responsible for the patient's location. This is possible because the user's request for assistance message includes an indication of the location of the user that initiates the request for assistance.

The request for volunteer citizen responders can also be initiated by an emergency services call center in response to a call for emergency medical assistance. By way of example, FIG. 2C is a flow chart illustrating a flow suitable for generating an alert to nearby public responders and AEDs that is initiated based on a call made to an emergency operators at a Public Safety Answering Points Center (PSAP Centers—e.g., a 911 call center in the U.S.) in accordance with one embodiment. In the illustrated embodiment, the process begins when a call is made to emergency operators (e.g. a 911 dispatcher) as represented by block 251. The call may be made by a witness or bystander to a potential cardiac arrest incident and the call effectively activates the emergency response process. Regardless of whether the caller witnessed the cardiac arrest incident or is told to call emergency services by another party, calling for help ensures professional first responders are dispatched to the emergency as quickly as possible.

Although it is expected that in most circumstances, the call to emergency services will be initiated by a person, in some instances, the call may be automatically initiated by an AED itself. For example, some AEDs may be designed to automatically initiate a call to emergency services when the AED is activated in an emergency mode or based on some other triggering event such as a user input, the detection of the opening of an electrode pad cartridge, detection of the placement of electrode pads, the detection of a shockable cardiac rhythm, etc.

When the emergency operator answers the phone, the operator undergoes a process of assessing the type of emergency for which the reported party is calling as represented by block 253. When appropriate, the operator will dispatch emergency services to the scene. In some jurisdictions, the operator helps the caller assess the patient's status to better understand the type of aid that may be required. For instance, if the patient is unresponsive and not breathing properly, the operator may infer that it is possible that the patient has experienced a sudden cardiac arrest. In such circumstances, the operator may guide the caller through steps of performing CPR and obtaining an AED, if one is present. In parallel, the operator will dispatch emergency services. Additionally, during the call, the operator asks and learns other important details from the caller, such as the location of the patient. In some circumstances, the patient location is determined by asking the caller. Additionally, many phones, including cellular phones have the ability to automatically provide their location to emergency services.

Details about the incident including information provided by the caller, the operator's assessments, the patient's location and other relevant information is commonly entered by the operator into an incident record in a computer aided dispatch (CAD) system. The CAD system shares the incident record with emergency responders, which helps speed up the dispatch process. It also helps professional first responders learn about the patient's status so that they have some understanding of the situation before they arrive at the patient's location.

In some implementations, the emergency operator may initiate a request for public assistance when appropriate as represented by the left branch of FIG. 2C. During the assessment referenced above, the emergency operator can determine whether an AED would likely be useful in the present circumstance as represented by decision block 255. Some key indicators of sudden cardiac arrest include descriptions of the patient being unresponsive and not breathing normally. If the emergency operator realizes that the patient may have suffered a sudden cardiac arrest and there is no AED on the scene, the emergency operator may initiate a request for public assistance via the CAD system as represented by block 259. Such a request may be initiated by selecting an appropriate GUI button or other GUI construct on the CAD system display. The request is forwarded to the AED response network server 20 which initiates a request for public volunteer responders as described above with reference to FIG. 2A.

It should be appreciated that most calls to emergency call centers do not relate to potential cardiac arrest incidents and therefore there is no reason to activate the AED responder network. For instance, if the emergency is described as a house fire or a burn victim, an AED wouldn't be useful. In such circumstance, the call would be handled in a normal manner without activating the AED responder network as represented by the "no" branch from block 255. Since the subsequent operator actions are not particularly relevant to the present disclosure, the process is effectively done from the standpoint of the AED responder network as represented by block 257.

The described emergency operator initialized call for public assistance can work very well in circumstances where the controlling authority is comfortable with the operators making an explicit decision regarding whether to request assistance from the AED volunteer responder network. However, some jurisdictions may prefer to have that decision made more automatically. One such automatic approach will be described with reference to the right branch of FIG. 2C—steps 262-268.

In this approach, the CAD record is analyzed to determine whether an AED would likely be useful as represented by block 262. This analysis can be performed in a variety of ways. For example, many CAD records have a number of tags that can be helpful in categorizing the incident or otherwise include an overview of the situation. A couple of the characteristics that are most relevant to sudden cardiac arrest are that: (1) the victim is unresponsive or unconscious; and (2) the victim is not breathing or not breathing properly. When the CAD record has specific tags for these conditions, the record tags can be searched and the incident can be categorized as a potential sudden cardiac arrest or not based on the tag search. If the incident is not categorized as a potential sudden cardiac arrest, then an AED would not likely be useful. If it is determined that an AED would likely not be useful as represented by the no branch from decision block 264, no further analysis of the CAD record would be necessary and the process is done from the standpoint of the AED responder network.

Alternatively, if it is determined that an AED may be useful (the yes branch from decision block 264) and the record further contains useful victim location data, a request for public assistance may be automatically initiated by the system as represented by block 268 including the patient's location. The request is forwarded to the AED response network server 20 which initiates a request for public volunteer responders as described above with reference to FIG. 2A.

In the simple example above, a couple specific CAD record tags were searched for to determine whether an AED might be useful. In other situations considerably more logic can be used to make that determination. For example, in some circumstances the operator may have asked and noted whether an AED is currently available at the incident location. If an AED is already on scene, there may be no reason to ask volunteers responders to bring an AED to the scene. However, in such a circumstance it may still be desirable to request volunteer assistance, although the volunteers may be asked to proceed directly to the incident rather than obtaining an AED.

It should be appreciated that not all CAD records will include the specific tags referenced above and in such circumstances the record can be scanned for keywords and/or other tags can be used, and/or other analytic approaches can be utilized as appropriate to facilitate making the decision whether to request public volunteer assistance through the AED public responder network. For example, in some implementations, an analysis engine (not shown) can have a table of keywords that are searched for that are indicative of cardiac arrest and corresponding logic that makes the decision regarding whether to initiate a request for assistance through the public responder network. Of course, a variety of other criteria can be used as well.

The analysis of the CAD record or other available data can be performed at any of a number of locations. In some implementations, the AED usefulness determination and request for public assistance initiation responsibility can be incorporated into the CAD software so that the decision is made directly at the emergency call center based on the incident record. There are also emergency data clearinghouse services which take data from local emergency call centers and make that data available in real time as appropriate to a variety of different public safety and/or emergency services. In the United States, the most common such service today is RapidSOS. In some embodiments, the AED usefulness determination and automated request for public assistance initiation responsibility can be incorporated into the servers at such clearinghouses. In still other implementations, the record or select records or portions of records can be forwarded to the AED responder network server(s) for analysis at that location. In such embodiments, the records, or relevant portions of the records can be forwarded directly from the call centers or via an emergency services interface such as RapidSOS.

Figure 2D:
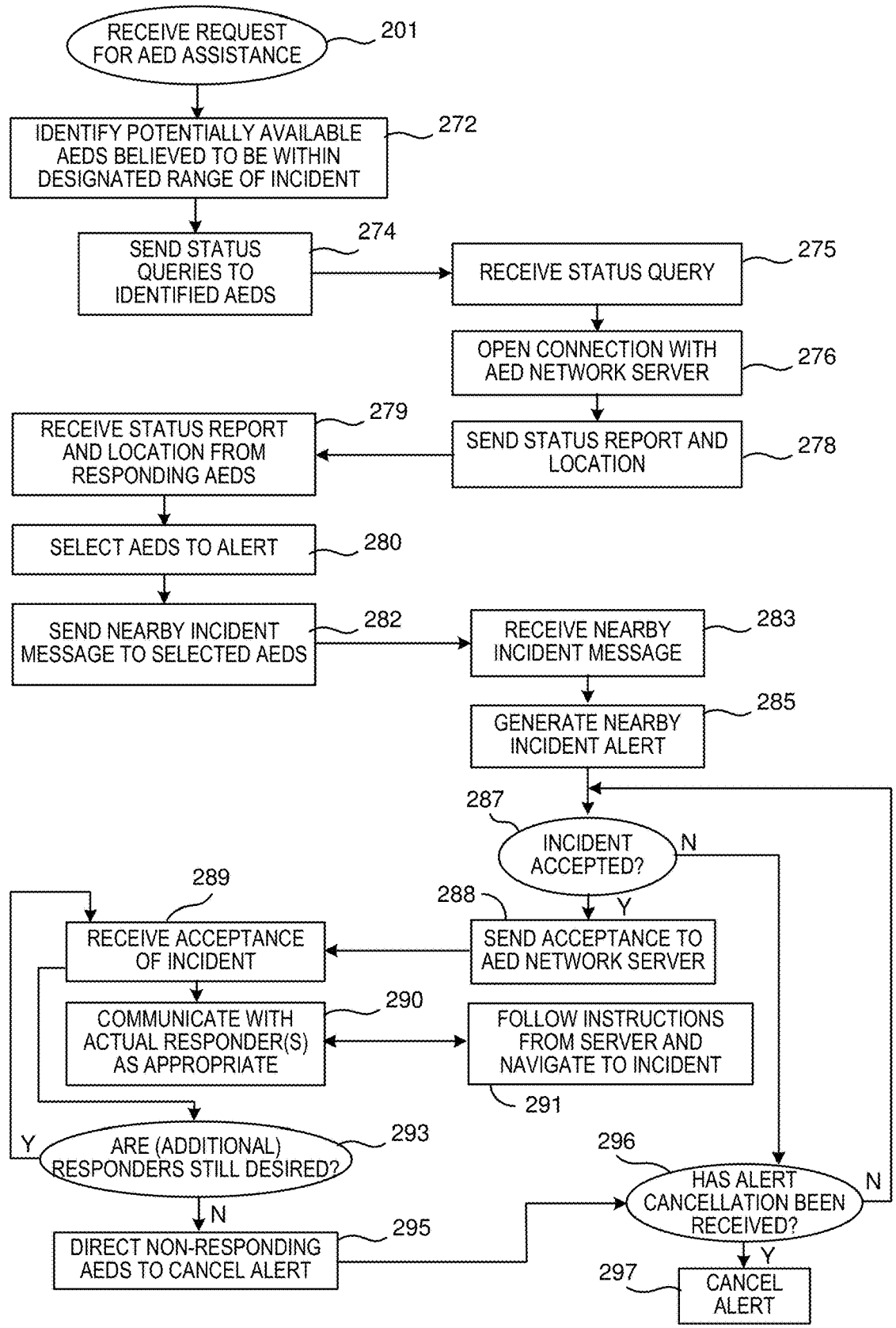
FIG. 2D is a flow chart illustrating another flow suitable for generating an incident alert to nearby volunteer responders and AEDs in response to a request for public AED assistance.

Referring next to FIG. 2D, another particular implementation of the AED notification process of FIG. 2A will be described. The embodiment of FIG. 2D begins when the AED response network server 20 receives a request for volunteer responders (block 201). In the described embodiment, the server 20 maintains a device database that includes records for each of the AEDs in its network. Some of the information stored about the AEDs may include information such as: (a) the device's geo-location; (b) whether the AED has been designated as a private AED or a public access AED; (c) whether the AED's administrator has opted in to receiving notifications regarding nearby potential cardiac arrest incidents; (d) whether the AED is designated as a mobile AED or is expected to be stored at a fixed location; (e) the current status of the defibrillator, etc. Preferably, the status and location information is updated on a regular basis, as for example as a result of periodic (e.g., daily) self-test status checks that are reported by the AED to the server 20.

When the AED is designated as a public access AED, the devices owner/administrator may designate the hours/days/etc. that it is available to the public. For example, if the AED is located inside an office building or retail establishment that is only open during designated hours, it may be desirable to indicate that the AED is only publically available during those hours so that potential $3^{rd}$ party responders don't try to find an AED in a locked building.

In general, nearby incident messages may be sent to any AED that has opted in to such notifications. That may include both public access AEDs that are available to the general public, and private AEDs which may not be advertised as being available to the general public. There are many circumstances where a private AED may elect to receive notifications of nearby incidents. Once such example may be when the AED is a personal AED of a volunteer responder. Another such example may be when the AED is located in a building or complex that is not publically accessible. Another example is when the AED is located in a person's home.

An AED may also be designated as a fixed location AED or a mobile AED. Fixed location AEDs are expected to be stored at the same location all/most of the time. In contrast, mobile AEDs are expected to be moved more often. Some representative examples of mobile AEDs might include AEDs expected to be kept in a vehicle or carried as part of a safety kit (e.g., by a coach, guide or volunteer responder).

It is expected that most public access AED would be fixed location AEDs that are expected to be stationed at a fixed location (e.g., in an AED cabinet at an office building, at a field, at a designated location in and airport, etc.). However that is not a requirement, for example, a police department might choose to designate AEDs carried in police vehicles as mobile, public access AEDs so that their locations can be displayed on an AED map in the event that the officer happens to be nearby when a potential cardiac arrest incident occurs. Of course, in other circumstances it may be desirable to designate such devices as private.

Returning to FIG. 2D, when the AED response server 20 receives a request for volunteers responders (block 201), the request includes the geo-location of the incident. The AED response server then identifies a set of AEDs that are potentially available to use in responding to the incident. The set of potentially available AEDs may be determined in a variety of ways using a variety of different filtering techniques. In some embodiments, the set of potentially available AEDs is determined at least in part by identifying the AEDs in the responder network database that are understood to be within a designated range of the incident based on the last known location of the AED as stored in the device database. (Block 272). In some implementations, the fixed range threshold is used in all circumstances, while in others the designated range threshold may vary based on a variety of factors. For example, in some implementations, the permissible range allocated for devices registered as mobile AEDs may be larger than the range allocated for permanent AEDs. This can be desirable because a mobile AED that is located in a vehicle may have traveled quite far since it last reported its status and location to the AED response server. In another example, when the incident location in a rural area that doesn't have a large number of AEDs, the range threshold may be larger than when the incident location is within a metropolitan area having a large number of registered AEDs. The specific range thresholds used in this initial identification of potentially nearby AEDs may vary widely. In some situations, this initial filtering may be quite broad (as for example, 50 or 80 miles in some applications) or it may be significantly more focused (e.g., a few miles or less) as may be appropriate for any particular setting and/or class of registered AEDs. In some embodiments, additional or other filtering may be used to identify the set of potentially available AEDs.

In step 274, a status query or "check-in" message is sent to each of the identified AEDs or to any desired subset of such AEDs. (Block 274). This is sometimes referred to as "pinging" or "polling" the AEDs. The pinged AEDs each respond with a "current status" message that provides their current location and operational status. (Step 278). This gives the AED response server the latest information about the identified AEDs and effectively verifies that communications with the devices is possible. The specific current status information transmitted may vary widely, but it preferably includes at least the device's current location and operational status. The operational status reported may include the results of the most recent status check performed by the AED. Such a status report may be very simple (e.g., functional/non-functional) or it may include more detailed information such as (but not limited to) battery charge level, pad expiration date, recent self-test results, etc. It should be appreciated that the amount of data transferred in the original request (the "check-in" message) and the response (the current status message) are quite small and can therefore be transmitted back and forth quite quickly. The messages may be transmitted using any of a variety of communications protocols supported by the AEDs, including, for example, as SMS messages.

In some embodiments, the AED receiving a status query (block 275) responds to the query by establish a connection with the AED response network server 20 over a second communication channel that is different than the first communications channel over which the status query is received. (Block 276). The current status message is then sent over this second communication channel. (Block 278). In some embodiments, the first and second communications channels use different communications protocols, although this is not a requirement. For example, the status query may be sent/received using a messaging technology (e.g., SMS), whereas the connection may be established using another communications protocol such as an IP protocol (e.g., TCP/IP). There are some significant advantages to such a separate channel approach from a security standpoint as described in more detail in U.S. provisional Application No. 62/895,071, filed Sep. 3, 2019, which is incorporated herein by reference. Although the separate channel approach works particularly well and has some distinct advantages, it is not required in other implementations.

As the AED response network server receives current status messages from the pinged AEDs (block 279), it effectively develops an updated AED map with the current location and operational status of AEDs in the vicinity of the incident.

In some embodiments, a somewhat similar approach may be used to poll registered volunteer responders to determine/verify their current location and to verify that they their devices can be communicated with (when such location services have been consented to by the volunteer responder). Alternatively, if the volunteer has consented to other types of location services, the server may track or determine the volunteers' location in other appropriate manners. For example, most Smartphones support location services that allow users to set their preferred level of location sharing for each app. When a volunteer consents to always sharing their location with the AED responder network, the AED server may have ready access to the volunteer's current location and in such circumstances there may be no need to ping the volunteer's device to determine their current location. Similarly, if the volunteer happens to have the AED app open and has consented to sharing their location while using the AED app, then the server may know the volunteer responders location. In other circumstances, the AED responder network server may not have a practical way of determining the current location of a volunteer. In such circumstances a registered, expected, or last know region may be used to determine the likely location of the volunteer responder. Regardless of the locating approach used, the server may determine the location of nearby responders in parallel with its verification of the location and status of nearby AEDs.

With the location and operational status information in hand, the server 20 determines which connected AEDs and/or volunteer responders to send an Emergency Incident Nearby message as represented by block 280. In some embodiments this is accomplished by an AED/volunteer selection algorithm. The specific algorithms and protocols used to select the specific devices/responders to inform of a "nearby" incident may vary widely based on a variety of factors and the perceived needs of any particular implementation. For example, in some implementations, the Emergency Incident Nearby message may be sent to any and all volunteers/devices that are considered "nearby" the incident. The specifics of what is considered "nearby" may be widely varied. By way of example, in some embodiments, the Emergency Incident Nearby message may be sent to any volunteer/device that is within a designated radius of the incident. In such cases, the designated radius is preferably set such that a responder responding to the notification can readily get to the incident in time to be useful. In some embodiments, if no volunteers or connected defibrillators are known to be within a designated radius, then a notification may be sent to the closest known volunteers/connected defibrillator(s) as long as they are within a second (longer) distance of the incident. Of course, the designated radii may be different based on whether the incident notification is to a responder or an AED, whether an AED is a mobile or permanent AED, whether a volunteer responder is expected, known or believed to have an AED in their possession or a variety of other factors.

Preferably, any distances used in the initial identification of potentially available AEDs (block 272) is greater than any distances used in the selection of AEDs to be alerted (block 280). This helps ensure a robust pool of AEDs to select from and provides flexibility to immediately expand the geographic area in which AEDs are notified if there are no, or not enough, qualified AEDs in the initial field.

The selection of who to send incident alerts to can be based on a number of factors and rankings in addition to (or in place of) their distance from the incident. For example, it may be desirable to estimate the time it will take for the potential responder to reach the scene and utilize that knowledge in determining who the alert should be sent to. Such an estimate can be based on factors such as the responder's expected travel speed (e.g., would they likely walk, run, or are they in a car?), how fast are they likely to walk/run/drive to the scene, etc.), in addition to an estimate of the actual travel distance (or path) a responder is likely to need to travel to reach the incident.

In many cases, the path that a potential responder/AED may need to travel to reach an incident may be quite different than the straight line distance (radius) to the incident. For example, in a city, the responder may need to travel along sidewalks, roads or walkways instead of cutting through buildings or lots that they don't have access to. In the countryside, a river or other obstacle may prevent a responder from traveling a straight line to the incident. Thus, in some circumstances an estimation of the distance (or path) that each responder is likely to need to travel to reach the incident may be used in the distance determination rather than simply using a radius/straight line distance from the responder. Some such approaches are described in U.S. Provisional Application No. 62/834,137 which is incorporated herein by reference.

There is some evidence that it is counterproductive to send notifications to too many volunteer responders. This is believed to be due, in part to alert fatigue. Thus, if a lay responder responds to an incident only to see that they are the $5^{th}$ volunteer responder and their help is not really needed, they may be less likely to respond quickly to a subsequent incident alert. Thus, in some implementations, when multiple potential responders are within range of an incident it may be desirable or preferable to select a subset of specific responders to be notified first of a specific incident. That is, the initial incident alert is only sent to the selected set of responders and/or AEDs. If one or more of those responders accept the request to respond, then it may be that no further incident alerts are required for the incident. Alternatively, if none (or not enough of) the initially notified responders accept the incident, then notifications can be sent to a second set and so on as deemed appropriate. Such a second set could be all nearby responders or another subset in accordance with the desired notification protocol. Another criterion that can be considered is the volunteer responder's incident response history. For example, if a responder has been notified of prior incidents, did they respond to the earlier notification(s) or not? And if so, how quickly did they respond. In general, with other factors being the same, it may be more desirable to send an alert to an individual that has responded immediately to all previous alerts than an individual that hasn't or has less frequently responded to prior alerts.

Another factor can be whether the responder successfully used an AED in an emergency scenario before. This information can be useful because some studies have suggested that a lay responder who has previous experience reviving a person with an AED is statistically more likely to have a successful outcome than those who haven't had previous experience in a real cardiac arrest setting—possibly even exceeding the outcomes of trained medical personnel who have not had experience using an AED in a real emergency.

Yet another factor can be the responder's indicated training or experience level. For example many paramedics, EMTs, doctors and nurses have indicated a willingness to serve as volunteer responders when they are off-duty. Their expertise makes them particularly desirable responders.

The determination of which AEDs to send an incident alert to can be based on a variety of generally analogous criteria plus a variety of different more AED specific criteria. For example, factors such as travel path distance, and incident response history can be equally relevant for AED selection. The relevance of the incident response history can be appreciated by considering an AED that is stationed in a school office that has several people trained in AED use vs. an AED that is stationed in a lightly traffic lobby of a building. While notifying either or both can lead to a positive outcome in any particular case, a device that was successfully deployed in response to a previous Emergency Incident Nearby is statistically more likely to illicit a positive response in the future.

In addition, selected AED status information can be used in the AED selection as well. For example, when the AED response network server has status information about the potentially available AEDs, the server can use that information in determining whether the AED is an appropriate incident notification target. For example, if the AED is inoperable, it is eliminated from consideration. If the AED's battery is low or its electrode pads are old but likely operable, the AED's priority level may be reduced or it may eliminated from consideration if/when other viable options exist.

More generally, as discussed above, some AEDs are configured to periodically send status reports to a network server (e.g., responder network server 20) that indicate the AED's current location and status, including the results of the most recent status check. Similarly, AEDs pinged by the responder network server (step 274 of FIG. 2D) respond with a current status report. The contents of the status reports may vary, but any status indictors provided in the status report can be used in the selection of AEDs to be alerted (step 280 in FIG. 2D).

In some embodiments the status report sent by the AED in response to a status inquiry includes: (1) the AED's current location, which may be in the form of GPS coordinates or other suitable formats; (2) a serial number field that stores the AED's serial number; (3) a hardware version field that stores a hardware identifier AED that indicates the hardware version of the AED; (4) a firmware version field that stores a firmware identifier that identifies the firmware version currently installed on the AED; (5) an electrode pad field that stores a pad identifier that indicates the serial number of the installed electrode pads; (6) a pad expiry date field that stores an identifier that indicates the expiration date of the installed electrode pads; (7) a battery charge level field that stores a charge level indicator that indicates the AED's current battery charge level; (8) a pad type field that stores a pad type indicator that indicates the type of electrode pads that are currently attached to the defibrillator (optionally one of the states indicated by the pad type indicator may be no pads attached); (9) a paired device field that stores a paired device identifier that indicates whether the AED is currently paired with another device via a short range communication protocol such as Bluetooth Low Energy (BLE); (10) a functionality status field that includes a one or more identifiers that indicate the functionality status of the AED. In some embodiments this may be a simple identifier (e.g. flag) that simply indicates whether the AED is functional or not functional. In others the functionality status field may include a plurality of distinct identifier (which may be flags or otherwise) such as, (a) an expired pads identifier that indicates whether the electrode pads are expired; (b) a used pads identifier that indicates whether the electrode pads have been used (and therefore need replacement); (c) a self-test failed identifier that indicates whether the AED passed or failed its last self-test; (d) a battery low identifier that indicates whether the AED's battery is low. Of course, a wide variety of other status indicators may be included in the status reports and not all of the foregoing are required in any particular implementation.

Any of the information set forth above can be used in the AED selection algorithm which determines which AEDs to send incident alerts to. In general, there are some criteria that will cause an AED to be eliminated from consideration. These may include factors such as the AED is not functional, the AED failed its last self test, no electrode pads are connected, the electrode pads have been used but not replaced, the owner/administrator elected not to opt-in to nearby incident alerts, etc.

Others items may be used to increase or decrease the relative priority of the AED. The relevance of the AED's response history to prior Emergency Incident nearby messages has been previously discussed.

In general, an AED is expected to be able to deliver a number of defibrillation shocks when necessary (e.g. when the initial shock doesn't revive the patient). An AED with a low battery may be quite capable of delivering a, or a few, defibrillation shock(s), but if its battery level is such that it can't necessarily deliver a large number of shocks, other things being equal, it would be preferable to deploy an AED that does have such abilities. However, when an AED with a low, but still functional battery charge level is much closer to the incident than any other AED, it may be desirable to send an alert to the AED having the low battery in the hope that it can be brought to the incident and deployed more quickly than other available AEDs.

In another example, it is generally not desirable to deploy AEDs with expired electrode pads. However, if the only AEDs that are nearby have expired pads, it may be better to use an AED with recently expired electrode pads, than no AED at all. The AED selection algorithm can incorporate best practices in determining when an AED with expired pads should be eliminated entirely from consideration, and whether/how to weight the impact of (recently) expired pads in the AED selection process. Both the pads expired flag, and the pad expiration date can be useful in making such determinations.

Another potentially useful piece of information in the described status reports is whether the AED is currently "paired" to a nearby device using a short-range wireless communications protocol such as Bluetooth. The Applicant has proposed AEDs that can be managed via Smartphones or other mobile communications devices. When such a device is wirelessly connected for a management function, that may suggest that someone (e.g. a potential responder) is currently interacting with the AED and or in close proximity to the AED, which may increase the priority of that particular AED.

In some embodiments, the AED's owner or administrator registers the AED when it is purchased or placed, or at some later time. Preferably the registration provides information about the AED's availability to the responder network and such availability information can also be utilized in the selection process. For example, the owner/administrator may opt the AED in or out of nearby incident notifications. In parallel, the owner/administrator may themselves opt in or out of nearby incident notifications on their cell phone or other communication device(s). The AED may be registered as a public access AED or a private AED. Public access AEDs are typically available to the general public, and as such, their location may be shown to volunteer responders and/or on AED maps and volunteers may be guided to the public access AED's location to pick up an AED on their way to an emergency incident. Examples of public access AEDs may include AEDs positioned at public fields, within buildings such as airports that are generally open to the public, in building lobbies, etc. In contrast, private AED may be AEDs that are not generally available to the public—as for example a personal AED stored at the owners residence, AEDs located in buildings, rooms or other places that are off-limits to the general public, etc.

In many cases a public access AED may only be publically available during selected hours, e.g., business hours. For example, an AED in the lobby of a commercial building may only be "publicly" available during hours in which the building lobby is open. Therefore, as part of the registration process, the administrator of a public access AED may designate the hours of public availability, e.g., the hours of the day/days of the week that a building lobby that has an AED is open.

Many AEDs—and particularly most public access AEDs are stored in fixed locations. However, in other cases an AED may be "mobile" in the sense that it can be expected to move around over time. For example, some police departments have outfitted many of their patrol cars with defibrillators and such AEDs would be considered "mobile" AEDs. Of course, a variety of other AED owner may also keep their AED in a vehicle as well. Still others may keep their AED in a bag or medical kit that they carry with them at times. The owner/administrator may identify an AED as a mobile device or a fixed device as part of the registration process and/or the static/roving nature of the AED can be determined or inferred by the AED network via periodic status reports sent by the AED that report the AED's current geo-location. For example, an AED that reports the same location every day for an extended period of time might be designated as a fixed location AED absent registration to the contrary. Similarly, an AED that reports different locations on a regular basis may be designated a mobile AED. Its relative mobility may also be inferred based on the disparity of the location reports.

It can be useful to the responder network to understand whether an AED is mobile or static, as well as how mobile a mobile AED is likely to be for several reasons. For example, in some embodiments, the responder network server 20 estimates the likely response time as part of the determination of which AEDs to notify of a nearby incident. The knowledge that an AED is stationed in a vehicle and therefore can likely be driven to the incident can be very useful to the estimation of the response time.

A wide variety of different selections algorithms may be used to select the specific AEDs and/or volunteers to be notified of a nearby incident. In some embodiments, a weighting based multi-objective optimization or a smart user filter may be used in the selection process. Some such examples are described in the incorporated priority provisional application Nos. 62/928,329 and 62/834,137.

In some embodiments, the selection algorithm can calculate a desirability score for each responding defibrillator based upon a number of weighted factors and send incident alerts to higher scoring units. Scoring factors can include an estimated travel time to the scene, battery charge level, etc. The actual number of defibrillators selected by the selection algorithm can vary widely based on design goals. In some embodiments, all AEDs that exceed a particular desirability score threshold may be notified. In some circumstances a minimum and/or maximum number of AEDs may be notified and such numbers may vary as a function of the desirability score. In some circumstances, all AEDs within a designated range that meet basic criteria will be notified and when possible, others will be notified if some minimum hasn't been reached. Of course, these various approaches may be mixed and a variety of other approaches can be used as well.

In other embodiments machine learning may be utilized to train an AI based volunteer responder/AED selection engine that is used to select the specific AEDs and volunteer responders to notify of an incident. An advantage of the machine learning approach is that the selection model can be updated on a regular basis to improve its performance. Over time, the machine learning will inherently weigh factors it determines to have the greatest impact on positive outcomes more heavily over time thereby improving the selection engine's performance.

Although a few specific factors have been described, it should be apparent that decisions regarding what specific factors to consider in determining who and/or what device(s) should be sent a particular incident alert and the relative weighting of these and other factors can all be widely varied to meet the design goals of any particular system. By way of example, the incorporated U.S. Provisional Application Nos. 62/834,137 and 62/834,137 describes a variety of responder AED selection criteria including some of those referenced above and others in more detail.

Figure 4C:
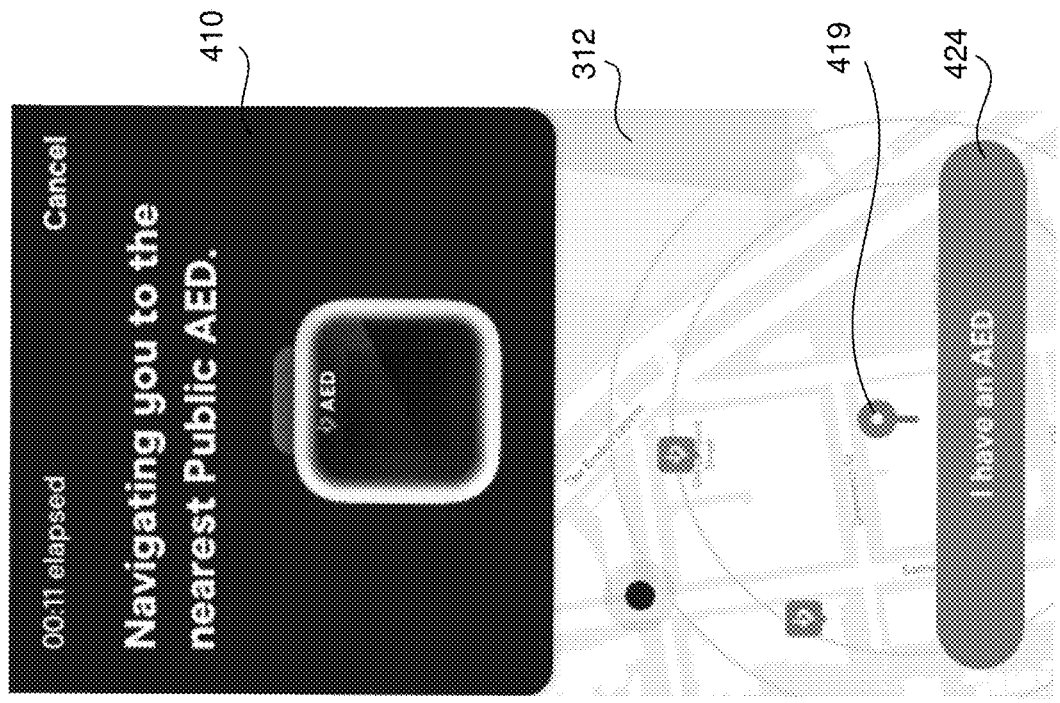
Figure 4B:
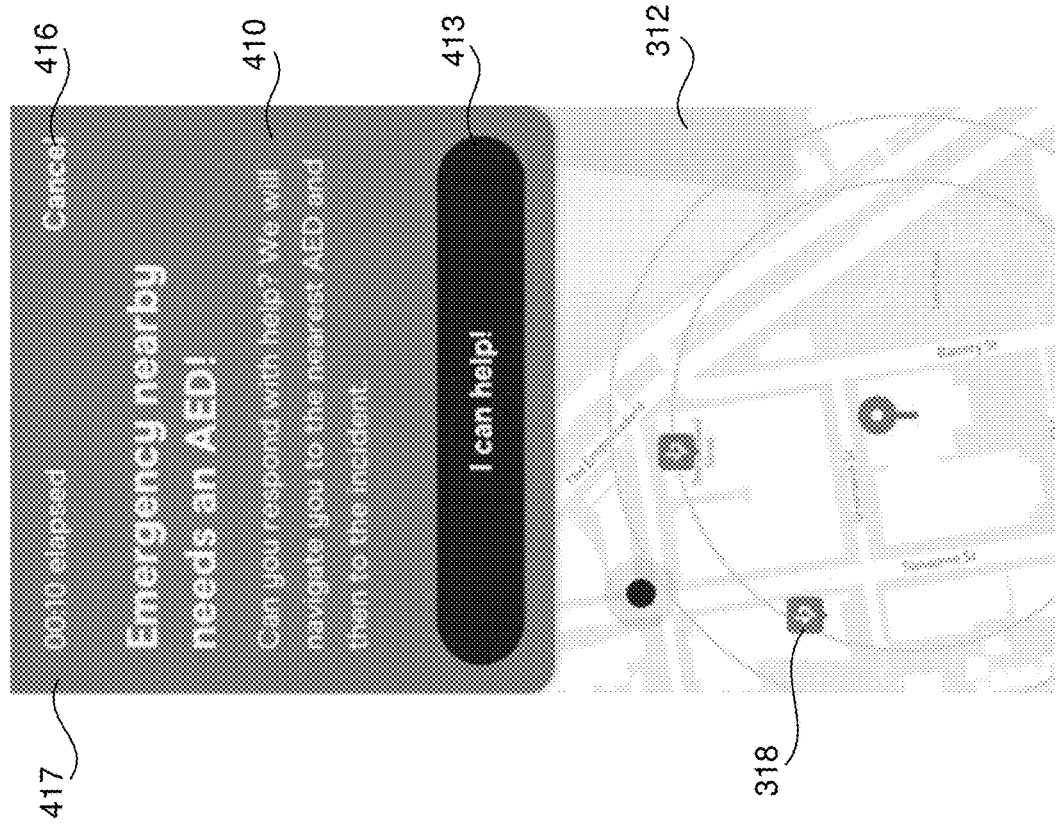
Figure 5A:
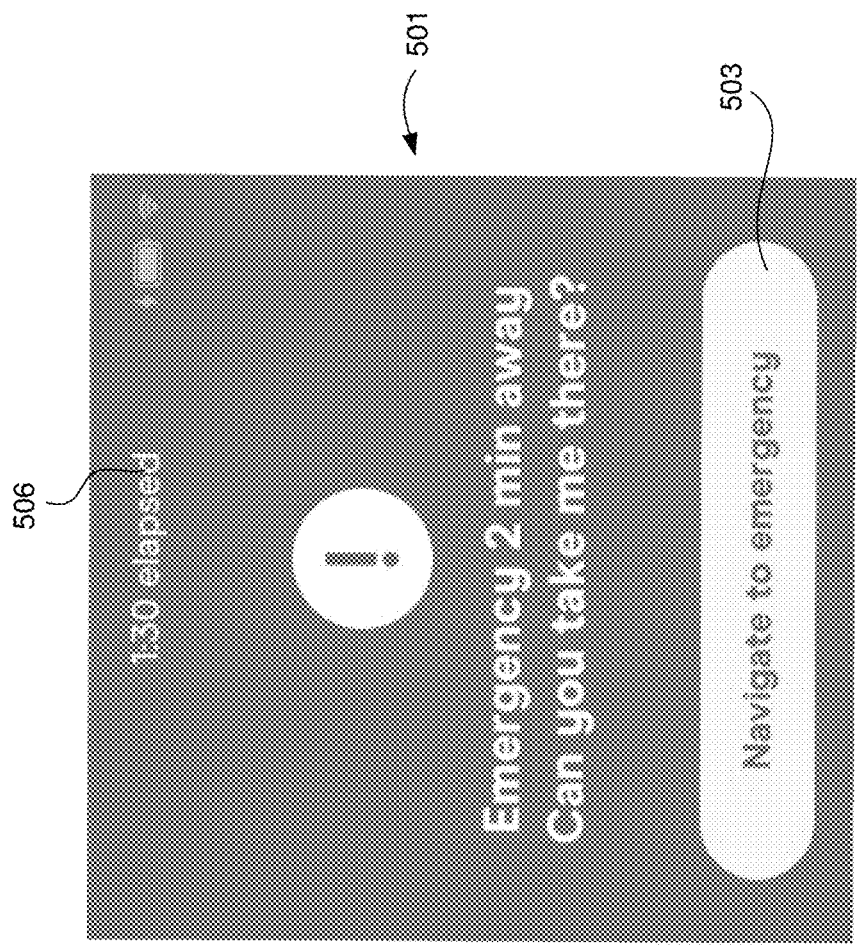
FIGS. 5A-5H are a sequence of cards illustrating a representative app flow and user interface suitable for use in a public access AED that is part of a public responder network.
Figure 4H:
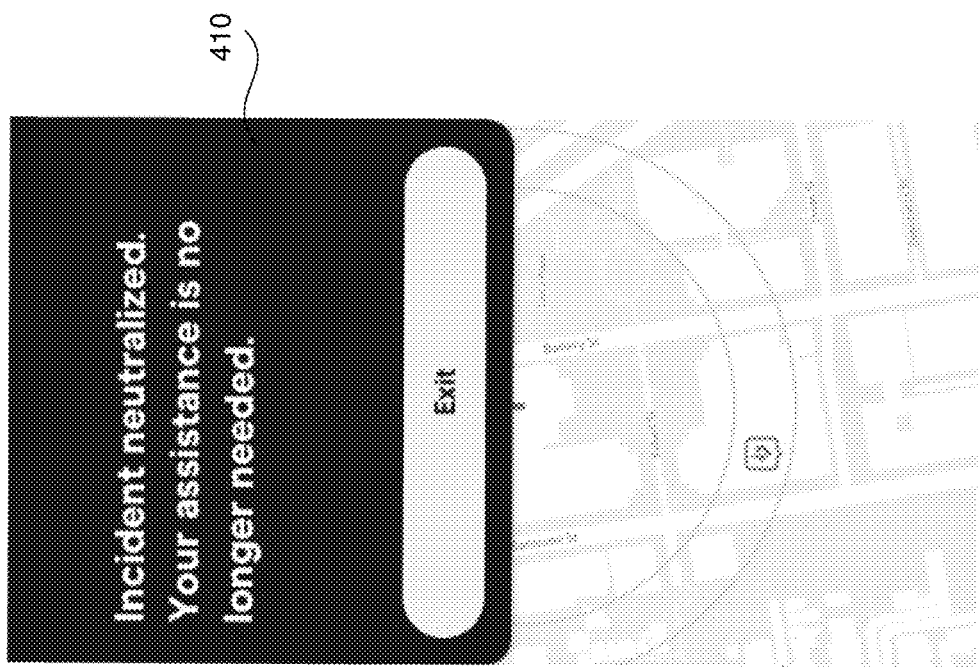

Returning to FIG. 2D, the server sends a nearby incident message to each of the AEDs that have been selected for notification (block 282) and each of the volunteer responders that have been selected for notification. In embodiments in which AEDs opened a connection with the AED network server 20 in response to the check-in status query (block 276), the nearby incident message may be sent over that communications channel. When a nearby incident message is received by an AED (block 283) the AED generates a nearby incident alert (block 285) as discussed above with respect to FIG. 2A. The alert preferably includes both an audio alert component, and a visual alert component displayed on a display associated with the AED. The visual alert preferably includes a card/frame/pane/etc that includes a GUI widget such as an accept incident button that when selected, informs the server that someone has picked up the AED and has indicated that they are responding to the incident. The specific text or graphics associated with the accept incident button or other GUI widget may vary widely, but when the incident is accepted (decision block 287) an incident acceptance message is sent to the AED server (blocks 288, 289). By way of example, in some specific interfaces described below, "I can help" button 413 in FIG. 4B and "Navigate to emergency" button 503 in FIG. 5A are good examples of suitable accept incident buttons. In other embodiments, the AED may be configured to understand spoken commands and the acceptance may be conveyed via a spoken response (e.g., a spoken "I can help").

Once the incident has been accepted, the AED response network server communicates with the AED as appropriate to direct the volunteer to the incident and respond appropriately (blocks 290, 291). By way of example, FIGS. 5A-5H show a representative sequence of cards illustrating an app flow and user interface suitable for directing a responder that has picked up an AED in response to a nearby incident alert.

The AED network server preferably monitors the incident as it progresses and will terminate the AED alerts if/when assistance or further assistance is no longer needed. When the server determines that responders (or additional responders) are no longer needed (block 293) the server sends a message to the non-responding AEDs to cancel their respective alerts. (Block 295). When an AED receives a cancel alert message (block 296) it will cancel the alert (block 297).

There can be a wide variety of different triggers that will cause the network server to cancel a nearby incident alert. For example, the emergency call 25 responsible for initiating a request for assistance may affirmatively cancel the request when it learns that: emergency medical personnel (e.g. an EMT, paramedic or ambulance) have arrived on the scene; or that other defibrillators have been brought to the scene; or it has otherwise been determined that an AED is not (or is no longer) needed. Similarly, a bystander at the incident who initiated a request for AED assistance using an app may cancel the request in similar scenarios. In other scenarios the AED network server itself may cancel the alert for any of a variety of reasons. For example, as suggested above, it may be desirable to cancel alerts generated by non-responding device after a designated number of AEDs and/or volunteers have indicated that they are responding to an incident.

In another example, a responding volunteer may indicate that they have arrived at the scene with an AED by selecting an appropriate GUI widget such as an "I've arrived" button on the AED display or on a volunteer responder's app. Once the AED network server has been informed that a defibrillator has arrived on the scene (or multiple defibrillators and/or volunteers have arrived on the scene if that is deemed preferable), the AED network server can send alert cancellation messages to the other alerted AEDs. If desired, AED alert cancelation decisions can be made independently of volunteer alert cancellation so that additional volunteer help can be requested even if addition AEDs are not required.

In another example, the AED may be configured to notify the AED server when it is deployed. In such circumstances, the AED network server can be configured to send alert cancelation messages when it is determined that a responding AED has been deployed at the incident location. Such notifications can be triggered by any of a variety of different actions, as for example based on any of (1) activating a "power on" button on the AED; (2) the withdrawal of the electrode pads from their storage location or the withdrawal of a pad cartridge from the AED; (3) attachment of the pads to a patient; (4) the detection of a cardiac rhythm, etc. Optionally, such notifications can include the location of the AED.

In some implementations, any AED that is picked up in response to a nearby incident alert may periodically transmit its location to the AED server 20. This is useful in helping the server provide appropriate instructions to the user. When such location updates are available, the AED server may be able to determine when an AED has arrived at the scene and base alert cancellation messages at least in part on such information.

Nearby incident messages that are sent to volunteer responders may be handled in a manner that is generally similar to the approach described above with respect to AEDs. FIGS. 4A-4H show a representative sequence of cards illustrating an app flow and user interface suitable for directing a registered responder to a nearby incident.

The nearby incident message may be sent to the volunteer responders using any of a variety of different technologies. In general, volunteer responders can be expected to have an AED or AED responder app on their cell phones or other mobile communications devices. Most modern cell phones have a notification service that can be used to push notifications to their users. For Apple devices incorporate the Apple Push Notification service (APNs) and Android devices include a Notifications service. Each of these services can be used to push a notification to a volunteer responder that will be displayed on the volunteer's device outside of the app's UI. The notification can be configured to either open the AED app, or take an action directly from the notification. For example, in some implementations, the message in the notification can be configured to allow the user to accept the incident directly from the notification by tapping on the notification or a specific button within the notification. Alternatively, a notification such as notification 402 in FIG. 4A may be configured to open the AED app when the volunteer taps on the notification, and more details about the incident and/or an incident acceptance button 413 can be presented in the app as illustrated in FIG. 4B.

In the description above, the status queries are described as being sent after the set of potentially available AEDs has been identified. Similarly, nearby incident messages are described as being sent after the AED Network Server has identified the AEDs to be alerted. It should be appreciated that these do not necessarily need to be linearly sequential steps. For example, if desired, the server can send status queries or nearby incident messaged to any selected AEDs as soon as that device is identified as a candidate, regardless of whether all of the potential candidates have been identified. To that end, it should be appreciated that due to factors such as network latency and device settings, there will sometimes be delays between the time a status query is sent and a responsive status report is received and it can be expected that the response times of different devices may vary—sometimes significantly. Thus, when desired, the selection of devices to send an incident alert to can be based on the information then available to the AED network server and may be updated by sending nearby incident messages to other AEDs and/or canceling alerts sent to other AEDs as appropriate as new information is received. In a specific example, any AED that is within a designated (relatively close) range of the incident can be sent a nearby incident message notified immediately upon the receipt of the status report or establishment of a connection.

Further, there may be circumstances where it is desirable to send a nearby incident message to selected AEDs based on prestored information. A good example of this is when an AED designated as a fixed location AED has recently updated its status and is known to be in good working condition. In such circumstances it may be desirable to send a nearby incident message to the AED immediately without first sending a check-in or status query if the AED has the ability to receive and process such messages (e.g., when the AED is not required to initiate the connection over which the nearby incident message is transmitted). Alternatively, such a nearby incident message can be sent immediately upon establishing a connection when a connection is required.

Referring next to FIGS. 3A-3G, a representative user interface that facilitates requesting help from nearly public responders from the scene of a potential cardiac arrest will be described. These figures show a sequence of cards that are appropriate for situations where a witness to a cardiac incident determines that a defibrillator may be required but is not present at the incident location. The described flow contemplates that the witness has an AED app (or other applicable emergency app) installed on their mobile phone or other readily available mobile communication device.

Initially the user (e.g., witness, bystander, etc.) activates the AED app on their mobile device which launches appropriately. In some embodiments, the initial card 310 that appears upon launch may be an AED location map 312 such as the map illustrated in FIG. 3A. Any of a variety of publically available mobile mapping services may be used as the platform for the location map 312, as for example, Google Maps, TomTom (used e.g. in Apple Maps), MapQuest, etc. The AED location map 312 has a location identifier 316 showing the user's current location and markers 318 that show the location of nearby public AEDs that are registered or otherwise known to the system. In the illustrated embodiment, the AED map includes an "Alert AEDs" banner 314 that serves as a call for help to nearby volunteer responders. In other embodiments the opening card or view may vary and the Alert AEDs functionality may be accessed in other manners.

Figure 3B:
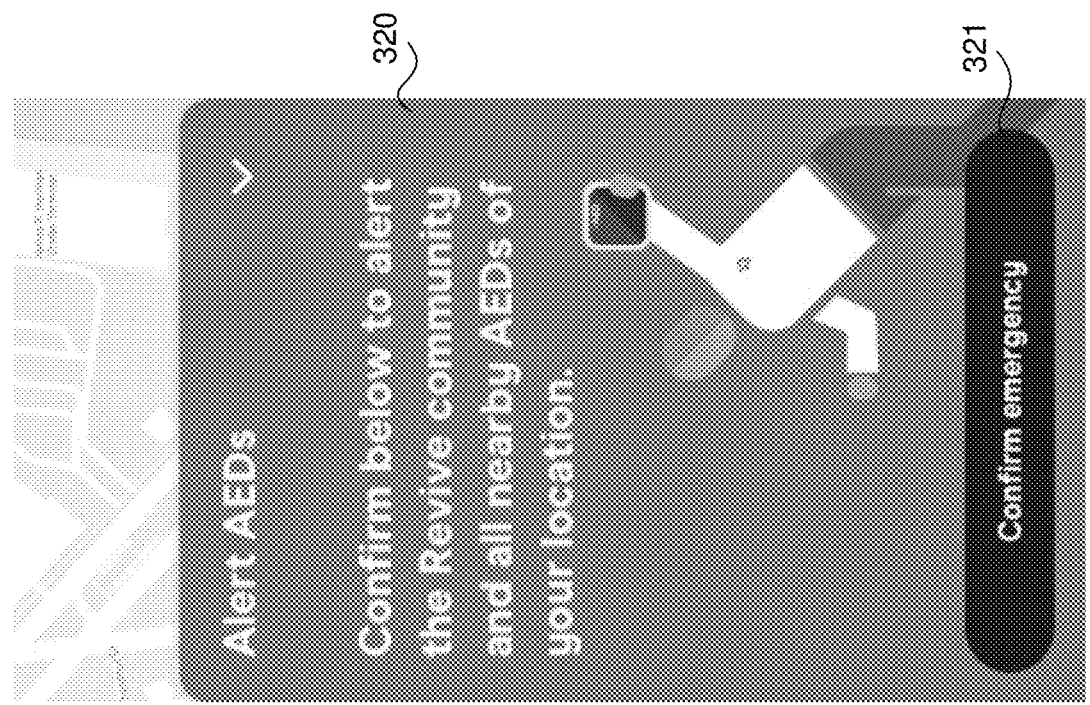
Figure 3A:
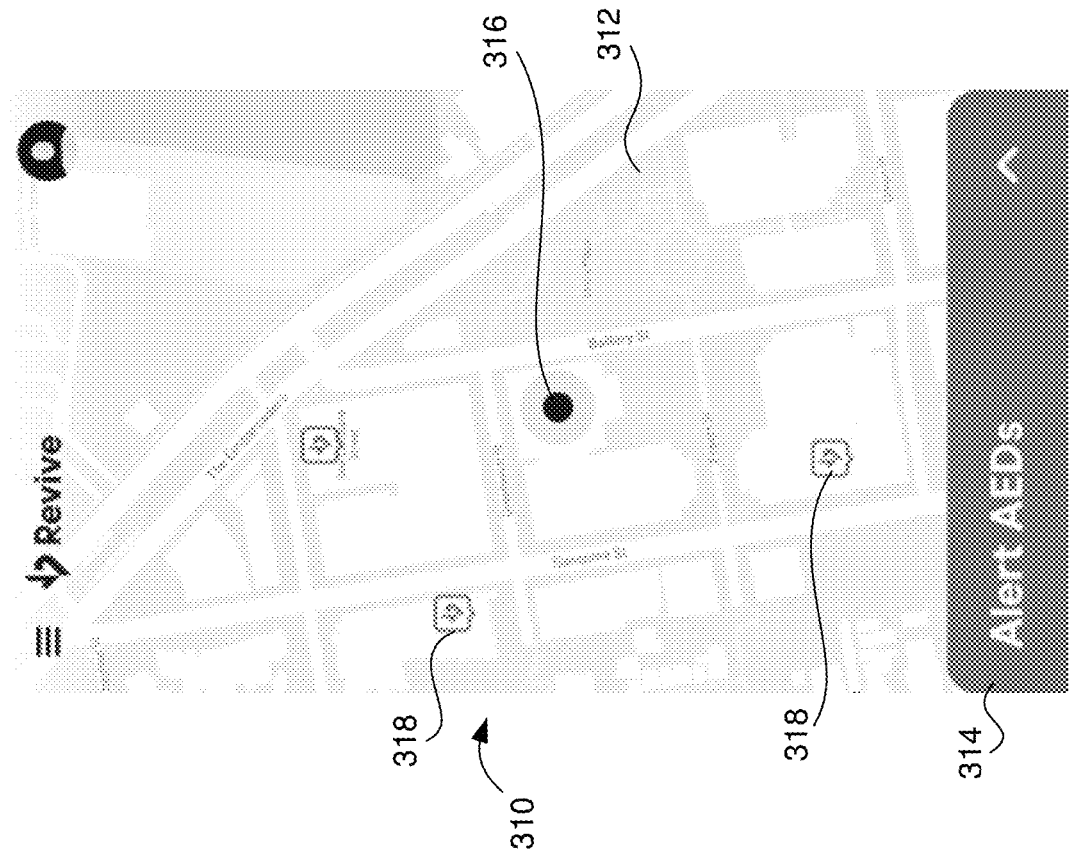

Selection of the Alert AED banner 314 causes the app to enter an Emergency Alert Mode and a confirmation pane 320 appears (or expands) requesting the user to confirm that this is an emergency as illustrated in FIG. 3B. The confirmation serves as a validation check to verify that the user truly desires to send an alert. In the illustrated embodiment, the desire to issue an alert can be confirmed by selecting the "Confirm Emergency" button 321. However, it should be appreciated that in other embodiments, a wide variety of other GUI input mechanisms may be used to confirm the intention to issue an alert. Selection of the Confirm Emergency button 321 causes a confirm location pane 325 to be displayed as illustrated in FIG. 3C. The confirm location pane includes a dialog box that presents the detected location of the user (and thus the emergency) and the user is requested to confirm (or correct) the displayed address and input any other location information that might be needed by a responder, as for example, the floor of a building, and/or the unit number in an office or apartment complex. Pane 325 also includes a "Confirm Location" button 328 that is selected when the user has confirmed the location.

Figure 3D:
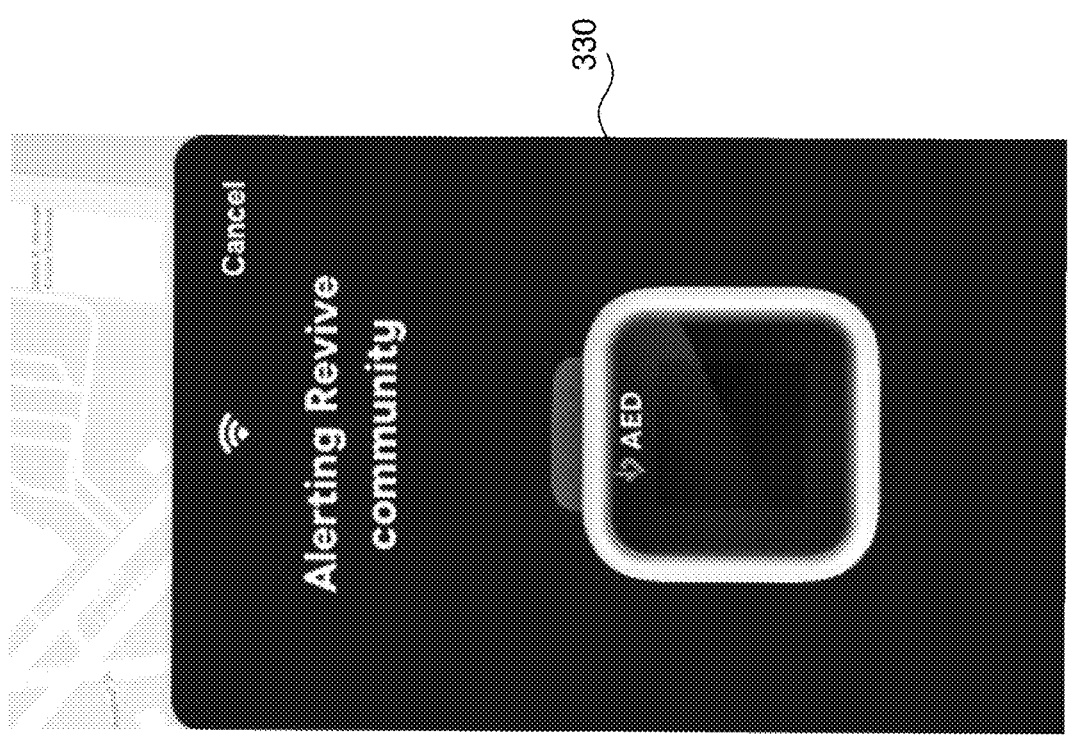
Figure 3C:
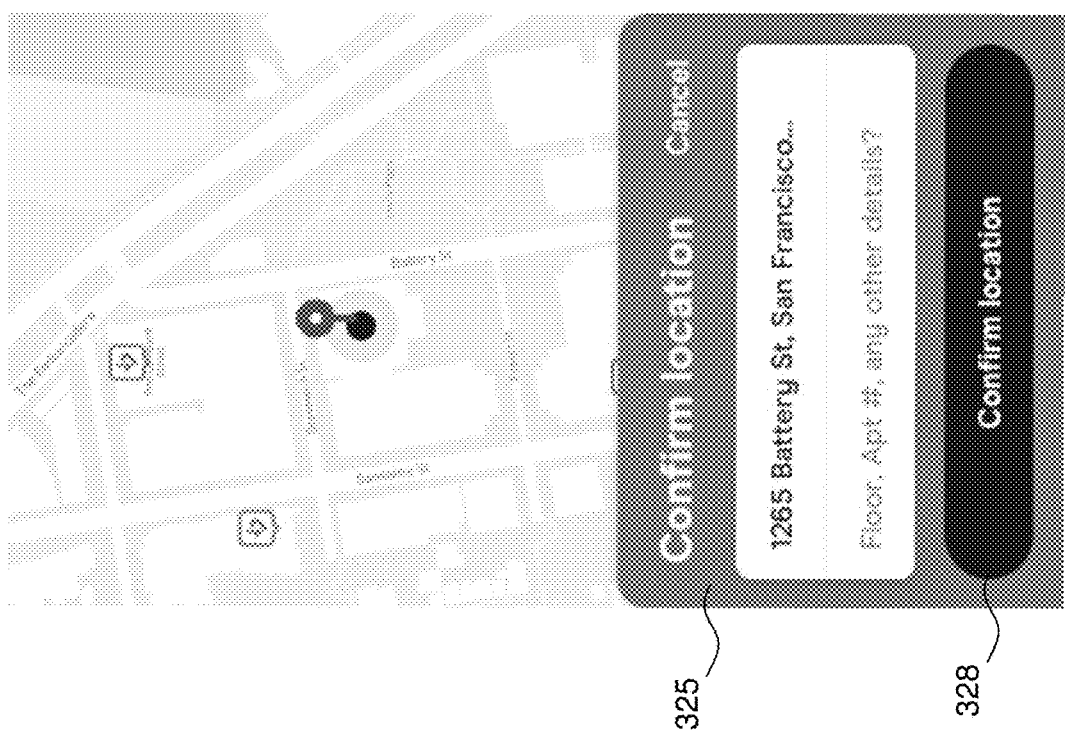

In the illustrated embodiment, the Alert is activated when the user selects the Confirm Location button 328 and an "Alerting Community" pane 330 is displayed to inform the user that an alert has been broadcast to the community as seen in FIG. 3D. In the primary described embodiment, the community includes registered volunteer responders and any alert capable AEDs that are perceived by the system to be close to the incident and therefore most likely to be capable of responding to the incident in a timely manner.

In some embodiments, each of the selections made by the user within the app are transmitted to the AED response network server 20 so the server has visibility of the potential cardiac arrest incident actions. When the server receives confirmation of the incident location it transmits the nearby emergency notification to registered volunteer responders that are close to the incident and transmits emergency alerts to nearby AEDs that are capable of receiving and reacting to such alerts. The AED response network server can use a variety of different selection criteria and selection algorithms to determine which volunteer responders and public access AEDs should be notified. For example, in some implementations responders and AEDs within a designated radius of the incident are identified as candidates (as for example within a two minute walk, etc.). If no, or very few (e.g. only one) volunteer responders are within the designated range then the range may be expanded somewhat in an effort to identify a (or additional) potential volunteer responder(s) that may realistically be able to get to the scene of the incident. A similar approach can be used for sending alerts to capable public access AEDs.

In some embodiments, the AED response network server 20 is configured to inform the appropriate traditional emergency services of the incident in parallel with notifying the volunteer network.

After the alert has been generated, the display may revert to the home screen (e.g., map card 312) as seen in FIG. 3E and a variety of features that may be helpful to the user may be displayed thereon. For example, the embodiment illustrated in FIG. 3E, includes a Live Update dialog box 341, a CPR Guide button 343, a Contact Emergency Services feature 345 and an exit button 347. The Live Update dialog box 341 provides the status of the alert and may be updated as appropriate at least until help arrives. For example, in the view shown in FIG. 3E, the notification in the Live Update dialog box informs the user of how many potential responders and/or AED were alerted and provides appropriate suggestions such as a direction to begin CPR. In some embodiments, the Live Update dialog box is updated as appropriate to show that a responder (or how many) responders (if any) have indicated that they are headed towards the incident with an AED. In some embodiments, the map 312 may be arranged to display the approximate location of such responders 348 and/or their progress as they move towards the incident as seen, for example, in FIG. 3F.

The CPR Guide button 343 or other suitable GUI interface provides a link to a CPR guide. When the CPR guide is activated it provides graphical and audio instructions on how to perform CPR. Contact Emergency Services feature 345 may take the form of a button or other GUI interface that when selected by a user will initiate a call to emergency services (e.g., 911 in the United States). It is generally expected that emergency services would have been contacted well before a user gets to this point, but the ability to contact emergency services from within the app can be useful because it allows emergency services to be contacted without requiring the user to exit the app. Exit button 347 provides a mechanism for exiting the Emergency Alert Mode and/or accessing other functionality of the App. In some embodiments, pressing exit button 347 causes a Confirm Exit pane with a confirm exit button thereon that is selected to exit the emergency feature.

Figure 3G:
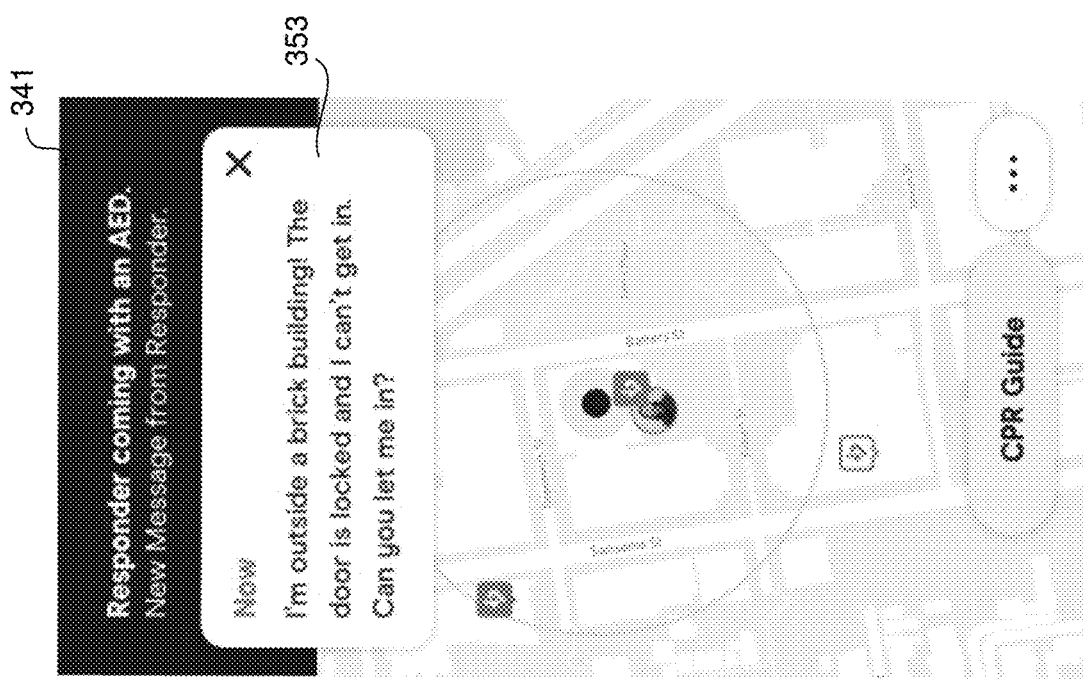

In some embodiments, the app is also configured to support some limited, in-app, messaging capabilities. Specifically, the app is configured to allow responders to message the person who generated the emergency alert if, and as, necessary. The content of such messages sent between individuals associated with the incident is sometimes referred to herein as "notes". In some embodiments, the only people that can message the initiator of the alert are persons (e.g., volunteer responders) that have affirmatively indicated that they are responding to the emergency nearby alert. In other embodiments, EMS responders may additionally or alternatively be able to message the person that generated the alert. In general, it is believed that it is desirable to keep any such messaging to a minimum so as not to distract the person that generated the alert—particularly when that person is responding to the incident—as for example by performing CPR. However, there are times when the ability to message may be very helpful—as for example, if the responder has arrived at the location, but is unable to get into the building, needs more specific directions regarding the specific location within a building, etc. A representative messaging interface is illustrated in FIGS. 3F and 3G.

In FIG. 3F, the message displayed in Live Update dialog box 341 indicates that a responder is on the way—which as discussed in more detail below, is a message that may be generated when a volunteer responder who received notification of an alert in their area confirms that they have received the alert and are on the way to the incident with an AED in hand. FIG. 3F also shows a message notification banner 351 that indicates that an active responder has sent a message to the alert generator. Selection of the message banner opens a message dialog box 353 that shows the message, as best seen in FIG. 3G. Of course, a variety of other GUI constructs can be used to access and/or show any received messages.

FIGS. 4A-4H are a sequence of cards illustrating a representative app flow and user interface suitable for notifying a registered responder of a nearby cardiac incident that can benefit from an AED and for guiding the responder's response to the incident. As discussed above with reference to FIGS. 2 and 3, when a witness to a cardiac incident or other appropriate source (e.g. emergency services) issues a push notification incident alert indicating that an AED is needed, the AED response network server 20 issues an Emergency Nearby Alert to registered volunteer responders who are believed to be within a designated useful range of the incident.

Figure 4A:
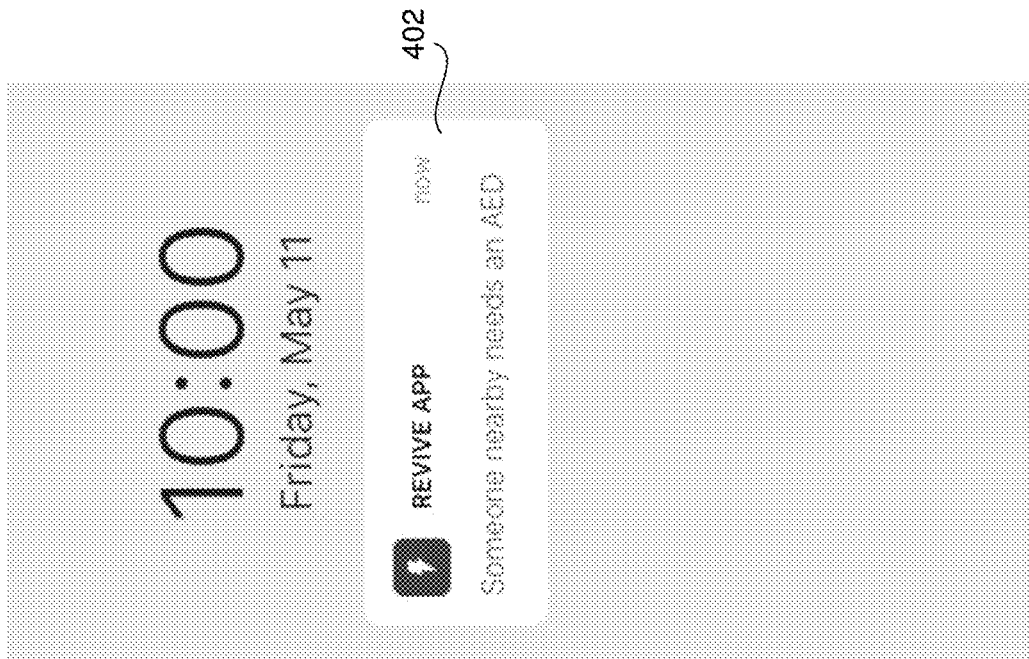
FIGS. 4A-4H are a sequence of cards illustrating a representative app flow and user interface for a registered responder receiving and responding to an emergency nearby alert via an app.

FIG. 4A illustrates a representative notification 402 that is displayed on the display screen of each notified potential responder's mobile phone or other device set up to receive such notifications. In some embodiments, an audio alert and/or vibration is generated together with the displayed alert to help draw the volunteer responder's attention to the notification. Typically, the user is able to select the nature of the sounds that are generated in response to an Emergency Nearby Alert via appropriate notification settings.

Selection of the notification 402 causes the defibrillator app installed on the responder's device to open or be brought to the foreground as appropriate. In the embodiment shown in FIG. 4B, a dialog box 410 is displayed over the base AED map 312. The dialog box 410 explains that there is an emergency nearby that needs an AED and asks whether the volunteer responder can help. A "willing to help" button 413 or other GUI interface is provided that may be selected by the notified responder to indicate that the responder is able to help. Alternatively, if the responder is not available to help, they may exit the response flow by selecting a cancel button 416 or other suitable GUI interface. A timing indicator 417 may optionally be provided to indicate how much time has elapsed since the alert was generated.

Figure 4E:
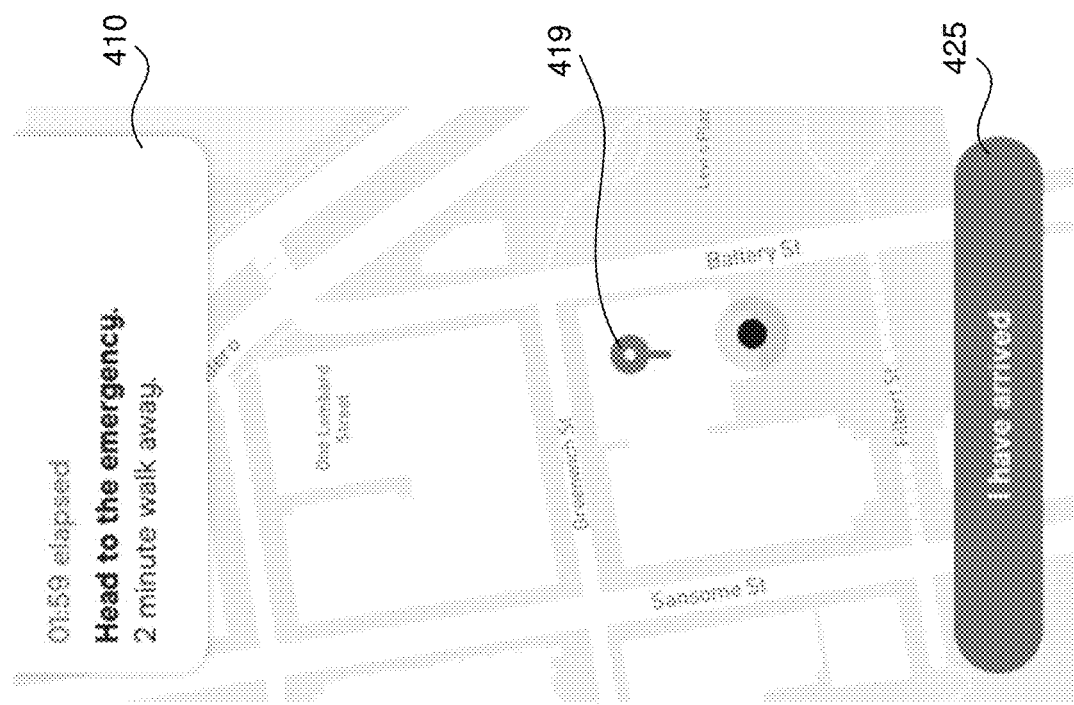
Figure 4D:
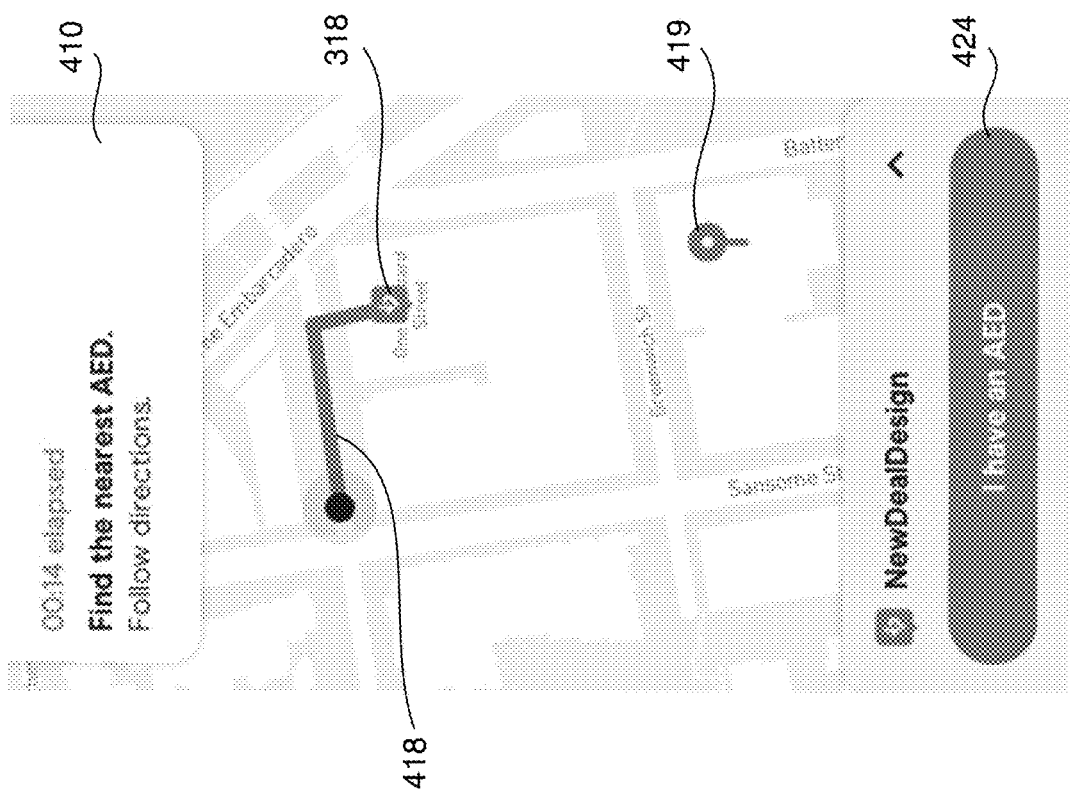

If/when the responder indicates that they are available to help, the map 312 may be updated to show an incident marker 419 that shows the location of the incident. The message in the dialog box 410 may be updated appropriately, as for example, to provide directions to a nearby publicly available AED, which may be the nearest publicly available AED. As previously mentioned, in some embodiments, the map 312 shows the location of any nearby registered AEDs 318. Additionally, directions 418 to the selected AED 318 may be displayed on map 312 as best seen in FIG. 4D. In some embodiments, the user can obtain details about the location of any registered public access AED (and other relevant information) by selecting the icon 318 corresponding to that AED.

In some embodiments, the response network server 20 is arranged to direct the accepting responder to the nearest available AED. However, in other embodiments, more, or considerably more logic can be used in the selection of the AED to direct the accepting responder to. For example, any of the logic used to select which AEDs to send nearby incident notifications to can also be used in the selection of which AED to send an accepting responder to. For example, the server may only, or preferentially, send responders to AEDs that have responded to a status inquiry sent after a request assistance has been received. Similarly, information in the status reports (or similar information previously known to the server) may be used in the selection of which AED to direct the accepting responder to. This can include information such as the defibrillator's operational status, battery charge level, electrode pad expiration status, or any other information in the status reports. In many implementations, the selection of the specific AEDs to send a responder to may be based on a number of weighted factors. By way of example, the multi-objective optimization algorithm described in the incorporated priority provisional application Nos. 62/928,329 and 62/834,137 works well. In other embodiments, a machine learning based selection engine may be used.

In some embodiments, the response network server 20 may be arranged to ensure that when more than one volunteer responder accepts an incident, or multiple responders accept different incidents, they don't get directed to pick up the same defibrillator. This can readily be accomplished by eliminating AEDs that have been allocated to another responder or are currently in use from consideration when allocating AEDs. Some may view this as important fearing that if a responder is directed to an AED that was just taken by another responder, confusion could occur and valuable response time may be lost as they try to figure out where else they may find a suitable defibrillator. Such confusion could also potentially diminish the responders trust in the system.

In yet other embodiment, whether the AED has been assigned to another responder may be a weighted factor in the consideration of which AED to direct the responder to. In such a system, the fact that the AED had been assigned to another responder may lower the probability that the AED might be considered, but not eliminate the AED altogether. Thus, for example, if an accepting responder is relatively close to two AEDs, with it being estimated that one will take 30 seconds longer to fetch and take to the incident, the system may direct the accepting responder to the further AED since the first AED may be picked up by another person and it wouldn't take too much extra time to pick up the second. At the same time, the system may permit directing more than one accepting responder to the same AED based on the realization that an accepting responder could potentially get lost, be unable to access the location, or abandon the response for a reason beyond the control of the system.

When multiple responders are directed to the same AED, it will often be desirable to keep the responders apprised of what is happening. This can take the form of informing other responders directed towards a specific AED if/when a first responder has picked up the target AED. At that time, appropriate follow-up directions can then be provide to the $2^{nd}$, etc. responders (e.g., go directly to the incident, try to pick up another AED, etc.). In some embodiments, when a volunteer is directed to a particular AED, that AED may be marked or displayed appropriately in the system (e.g., through the use of a different color or other distinguishing feature) so that others are aware of the situation. A mechanism is also provided to allow the user to indicate that they have an AED. In the illustrated embodiment, that mechanism takes the form of an "I Have an AED" button 424 or other suitable GUI interface. Once the responder has an AED in hand, they indicate that they have the AED be selecting I Have an AED button 424. At that time, they may be provided with directions to the incident as illustrated in FIG. 4E. In some situations, the responder will either have their own AED, or may already know the location of the nearest AED—and in such circumstances, they may select the "I Have an AED" button 424 to immediately see the directions to the incident.

FIG. 4E illustrates a representative user interface showing directions to the incident. In this state, the user interface may include an "I Have Arrived" button 425 or other GUI interface that permits the user to indicate to the server that they have arrived on the scene. In some embodiments, the "I Have Arrived" button only appears when the app detects that the responder is within a designated range of the incident.

Throughout the process, the messages provided in dialog box 410 may be updated to display messages that are relevant to the then current response state. For example, when the map 312 is displaying directions to the nearest available AED, the dialog box 410 may be updated to indicate that action as best seen in FIG. 4D. When the map 312 is displaying directions to the emergency, the message in the dialog box 410 may be updated to indicate that action as seen in FIG. 4E.

Figure 4G:
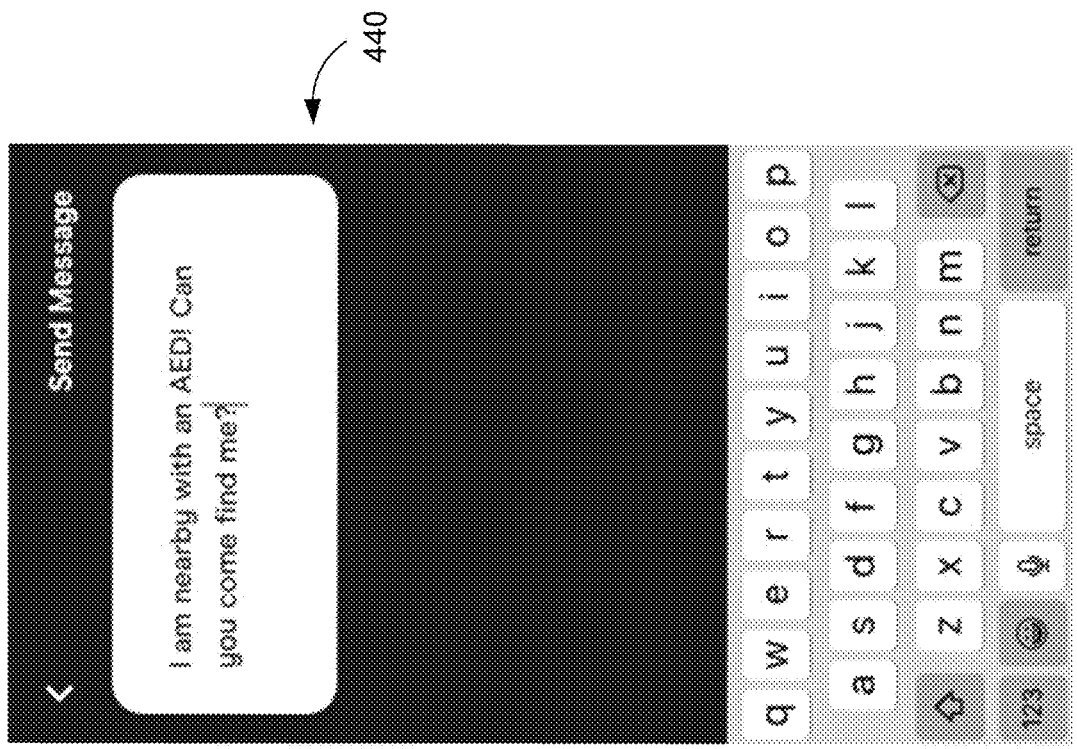
Figure 4F:
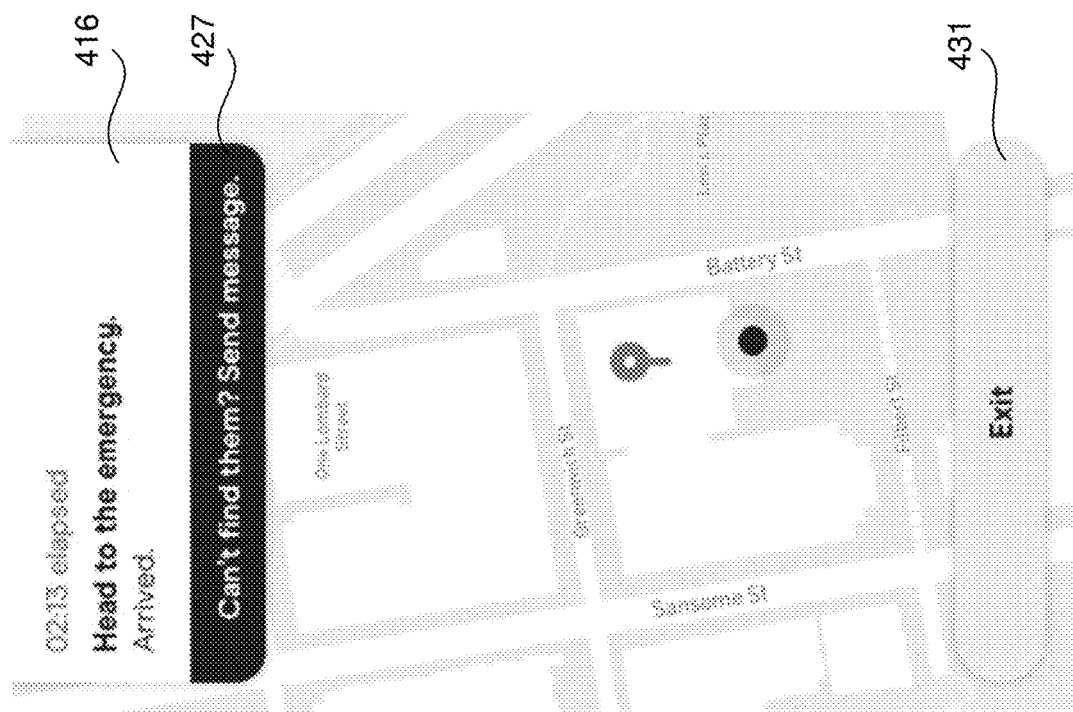

In some embodiments, a message button 427 may be provided to allow the responder to directly message the initiator of the emergency situation as seen in FIG. 4F. The specific circumstances in which messaging is permitted may be varied based on the design goals of any response system. For example, in some embodiments, direct messaging may be permitted at any time after a responder has indicated that they are responding to the incident. However, in other circumstances it may be desirable to more strictly limit the availability of messaging from volunteer responders to reduce the probability that the initiator of the request for help will be distracted from administering CPR or otherwise attending to the victim. Thus, for example, in some embodiments, the messaging functionality may only be activated once the responder is within a given distance of the victim or within some other designated threshold.

When the messaging button 427 is selected, a messaging interface is displayed that allows the responder to directly message the initiator of the call for help as illustrated in FIG. 4F. Any of a variety of conventional messaging widgets can be use to provided the messaging functionality. One representative messaging interface 440 is illustrated in FIG. 4G.

Once the responder has arrived, they can exit the emergency at any time by selecting an exit mechanism. As seen in FIG. 4F, the exit mechanism may take the form of an exit button 431 or other suitable GUI interface.

In some circumstances the initiator of the request for help may cancel the request for help before (or after) a volunteer responder arrives. This may be due to the arrival of emergency medical services or another volunteer responder. If the request for help is cancelled, other responders may be notified of the cancelation via an appropriate message in the dialog box 410 as seen, for example, in FIG. 4H.

FIGS. 4A-4H illustrated an app flow suitable for notifying volunteer responders of a nearby emergency incident in which help is needed and for guiding accepting volunteer(s) to the scene. In some embodiments, emergency incident alerts may also be sent directly to connected defibrillators that are physically located nearby the declared emergency.

Referring next to FIGS. 5A-5H, a representative app flow and response to the emergency nearby alert from the standpoint of a public access AED that is part of a public responder network and located near the incident will be described. In this embodiment, when an emergency incident alert defibrillator help request is received by the AED response network server 20, the server identifies any AEDs that it understands to be located nearby the incident. The server then sends an "Emergency Incident Nearby" message to each accessible defibrillator that is understood to be close to the location of the incident.

When an Emergency Incident Nearby message is received by a defibrillator it triggers an app installed on the defibrillator to enter an emergency nearby mode that is configured to: (a) inform nearby personnel (potential responders) of the existence of the emergency/request for help; and (b) direct anyone responding thereto to the location of the incident.

In some embodiments, when an Emergency Incident Nearby message is received, the app will cause the defibrillator to issue an alarm that can be perceived by potential responders that may happen to be close to the defibrillator. The alarm issued by the defibrillator may vary widely. For example, in some embodiments, the notified defibrillator activates its display screen and displays an Emergency Nearby message frame indicating the occurrence of a nearby emergency incident and a prompt encouraging the responder to take the defibrillator to the site of the emergency. One such Emergency Nearby message frame is illustrated in FIG. 5A. The alarm is preferably delivered in a manner that is likely to draw attention to the defibrillator. In some embodiments, this can include flashing the Emergency Nearby message, or other actions to draw attention to the defibrillator's display screen. In some embodiments, an audio alert may additionally or alternatively be provided. For example, a series of beeps or other sounds may be played to attract attention to the defibrillator thereby encouraging bystanders to view the displayed message and/or otherwise informing potential responders of the incident. In other embodiments, the audio alert may take the form of a spoken message.

In the embodiment illustrated in FIG. 5A, the Emergency Nearby Message frame 501 includes a GUI button 503 or other GUI element that provides access to a navigation frame 510. In some embodiments, the Emergency Nearby Message Frame 501 may also include a timer 506 that displays the time that has elapsed since the call for help was made. Selection of the button 503 in the Emergency Nearby Message frame causes navigation frame 510 to be displayed. The navigation frame 510 shows the user how to navigate to the emergency incident. In the embodiment illustrated in FIG. 5B, the navigation frame 510 includes a map 512 with path 513 shown from the defibrillators present location 514 to the incident 516. The navigational frame 510 may also display a dialog box 515 that displays instructions 517 that inform the user what to do until arriving at the emergency location. If desired, the displayed map, the present location and/or the instructions 517 may be updated appropriately as the user progresses towards the incident. In various embodiments, the map may be configured to display other information of interest as well—as for example: step-by-step instructions regarding how to get to the incident (not shown); an estimate of how long it will take to get to the incident 518; the timer 506 that displays the time that has elapsed since the emergency was declared, etc. In some embodiments in which the map has GPS or other position sensing capabilities, the map may also include a location marker that moves with sensed movements of the defibrillator to show the users progress towards the incident (not shown).

When the user arrives at the scene or is very close to the scene, the information displayed in the Navigation frame display may optionally transition to an "Arrived" frame 520 which may provide somewhat different information. By way of example, in the embodiment illustrated in FIG. 5C, the map 512 is still displayed but the instructions 517 may change to indicate how to begin use of the defibrillator and/or the path 513 may be replaced by a label 523 indicating that the defibrillator has arrived on the scene. Alternatively, the display may automatically transition to emergency use/operating instructions (e.g., the "Pull red tab to start" frame illustrated in FIG. 5D).

In some embodiments the Navigation fame may display a GUI element that permits the responder to indicate to the system that they have arrived at the incident scene. This GUI element can take a wide variety of different forms, as for example, an "I have arrived" button (not shown). Selection of the "I have arrived" button may be configured to cause the AED to transition to displaying emergency use/operating instructions (e.g., the "Pull red tab to start" frame illustrated in FIG. 5D) and/or cause a corresponding arrived message to be forward to the AED response network server 20.

Either or both of the Navigation frame 510 and the Arrived frame 520 may also include a Message feature (not shown) that allows the user to send a message to the help requester as mentioned above and/or received messages/ notes from the help requester. This can be particularly helpful when the original message does not include all of the information that might be required to get to the scene. For example, if the incident has occurred in a multi-story building, the responder may need to ask what floor of the building to go to. If the incident has occurred in a locked building, the responder may need to ask the requester to let them in the building. Of course a wide variety of other messages may be useful or appropriate in other particular circumstances.

In some embodiments, the navigation frame 510 may also have an "Activate Defibrillator" button or other GUI element that causes the defibrillator to transition to the emergency mode and the defibrillator app to transition to the emergency incident flow. Alternatively or additionally, in some embodiments, the emergency flow may be activated by performing an action on the defibrillator such as pulling a tab to access the electrode pads, pushing a mechanical button on the defibrillator, etc.

In some embodiments, the instructions 517 in dialog box 515 may include GUI buttons or other GUI elements that allow the user to access other information. For example, in the Arrived frame 520 of FIG. 5C, the instructions 515 include a button 526 that a user may select to get further instructions regarding how to activate the defibrillator as represented by frame 530 (FIG. 5D) which graphically illustrates that pulling an electrode pad cartridge tab starts the emergency sequence. Of course, a wide variety of other information (instructional or otherwise) can be made accessible to the user in a similar manner.

When the defibrillator is put to use for treating a cardiac incident, the display controller transitions from the emergency nearby flow to an emergency handling flow. At some stage the emergency use of the defibrillator (emergency session) will be terminated. The termination can be initiated via a number of different mechanisms, as for example by pressing a power on/off button on the defibrillator itself to stop the session, or by selecting an exit emergency GUI element displayed on the screen. At the termination of the Emergency session a Session Termination frame may be displayed. One representative Session Termination frame 550 is illustrated in FIG. 5E. In some embodiments, the Session Termination frame may include a prompt 552 encouraging the person possessing the defibrillator to return the defibrillator to its home location. In the embodiment illustrated in FIG. 5E, the prompt is part of a GUI button 554 or other GUI element that when selected causes a Return Map frame to be displayed. One suitable Return Map frame 560 is illustrated in FIG. 5F. The illustrate frame 560 includes a map 512 having directions to the defibrillator's home location 564. When the defibrillator is returned to its home location a button or other suitable element may optionally be selected to terminate the Emergency Nearby flow as illustrated in FIG. 5G.

If the defibrillator was actually used in the incident, the electrode pads will likely need to be replaced and other maintenance or attention may be desirable as well. Thus, after the defibrillator is returned to its home position or at any other appropriate time(s), any appropriate status notifications may be displayed on the display screen. FIG. 5H shows a representative status notification frame 570 which informs the owner and other interested individuals that the electrode pads need to be replaced. In the illustrated embodiment, the pad replacement status notification has links to useful information such as instructions or a tutorial on how to change the pads and/or to a mechanism for ordering new pads.

In the description above it is pointed out that the Emergency Incident Nearby message may be sent to any volunteer responders and/or connected defibrillators that are considered close to the incident. The specifics of what is considered "nearby" may be widely varied. By way of example, in some embodiments, the Emergency Incident Nearby message may be sent to any volunteer/device that is within a designated radius of the incident. In such cases, the designated radius is preferably set such that a responder responding to the notification can readily get to the incident in time to be useful. In some embodiments, if no volunteers or connected defibrillators are known to be within a designated radius, then a notification may be sent to the closest known volunteers/connected defibrillator(s) as long as they are within a second (longer) distance of the incident.

An AED app in the form of programmed instructions suitable for facilitating the described response system may be installed in memory on any smart phone, tablet computer, or other mobile communication device, and/or on any other suitable computing device. The programmed instructions may be configured to be executed by a processor (or multiple processors) provided by such devices.

Similarly, a defibrillator control app or other suitable defibrillator response software for facilitating the described defibrillator response system may be installed in memory of a defibrillator. The programmed instructions may be configured to be executed by a defibrillator processor (or multiple processors) or defibrillator controller resident on the defibrillator. In some embodiments, the defibrillator response system is part of a downloadable software app that is configured to be downloaded to memory on the AED and installed on the AED to be executed by the defibrillator processor or controller. Such an app based downloading and installation process greatly simplifies the ability to update the app's functionality (and therefore the defibrillator's functionality) in a timely and reliable manner.

In some situations, when the professional first responders arrive to the scene of a reported emergency, they might report the fact that they have arrived to the scene of the reported emergency to the dispatcher. In other cases, the first responders themselves may update the record for the emergency incident directly using an emergency dispatch product connected with the primary CAD system. Once the record for the emergency incident has been updated with information that professional first responders have arrived to the scene of the reported emergency, the CAD system may update the emergency incident record on the AED response network servers with this information. The servers might then report to the responders and AEDs in the network that there is no longer a continued need for service and emergency response.

AED Map Features

In some implementations the AEDs identified on the AED map may be marked, highlighted or otherwise identified in a manner that indicates the confidence that the AED is actually at its proscribed location. For example, in some implementations multiple categories may be identified. Some AEDs are connected devices with location identifying capabilities such as GPS. The system can have a high degree of confidence that such devices are actually located where they say they are because they are self reporting their location—which can be verified at any time. In some implementations, such AEDs can be woken up at regular intervals (e.g., once per day or other suitable time period) to run any appropriate diagnostics and report its location to the AED response network server 20. The diagnostics reports whether the AED is still in good operating condition, so the operational condition of the AED is also known. Thus, the AED response network server 20 knows both (a) where the AED is located, and (b) that it is in good working order with a high degree of confidence and such units can be displayed on the AED in a manner that indicates that high degree of confidence—as for example by showing the icon 318 that represents the AED on the AED map in a first color—such as red. If it is determined that the AED is not in good working order for any reason, then the AED can be removed from the AED map so that potential users aren't encouraged to go to find an inoperable AED. Similarly, if its location cannot be self-verified, the AED can be removed from the AED map unless its location can be verified by other means.

A second level of confidence may be applied to devices that are not themselves connected devices with location identifying capabilities but whose location and functionality can periodically be verified. One way to do this is to require the owner or an administrator to periodically pair a mobile phone or other mobile device executing a defibrillator app with the AED unit to serve as a conduit for transmitting information between the unit and the server. A wide variety of information can be transferred in this way, including, for example, communicating updated diagnostics reports to the server that can verify that the reporting device is still in good working order. For such devices, the location of the AED can be determined by the location of the paired device. Of course, the functionality and location of such devices can be verified in other suitable ways as well. In some implementations, devices that have relatively recently had both their functionality and their location verified can be shown in a second color—such as gray—on the AED map to graphically indicate the level of confidence the server has that the device is both functional and present at its designated location.

A third level of confidence may be applied to devices that are not capable of communicating their functional state to the server. The location of such devices can be reported by interested parties in any suitable manner—and such devices might be presented on the AED map in a third color or format. Of course, when appropriate, other categories or levels of confidence can be envisioned and represented on the AED map in any desired manner.

Emergency Call Center Integration

As suggested in some of the discussion above, there can be significant advantages to integrating the AED responder network with emergency call centers and such systems have been generically proposed in the past. However in practice, there are significant barriers to implementing such systems. One practical barrier is that there are a large number of emergency dispatch centers run or overseen by a wide variety of different entities. Therefore, they aren't standardized in their organization, processes and/or contracting practices. For example, different call centers may utilize different call handling processes, different event coding and/or may classify and structure event data in different ways. Still further, they may use different CAD system and their externally available APIs are not standardized.

The architecture proposed in FIG. 1B is particularly well suited for overcoming many of these barriers. Specifically, there are currently emergency service interfaces such as RapidSOS which provide an interface for providing a link for transmitting data from connected devices 29 to emergency services. Such interfaces have already integrated with (or are in the process of integrating with) a significant percentage of the emergency dispatch centers. In the embodiment of FIG. 1B, the AED Network Server 20 communicates with the emergency call centers 25 through the emergency services interface 28 which significantly simplifies the call center integration process.

In some implementations, the CAD system user interface is modified to include an Activate AED Network GUI widget that when selected, sends an Activate AED Network message to the emergency services interface 28. The emergency services interface 28, in turn forwards the Activate AED Network message (which serves as a request for AED assistance) to the AED responder network server 20. In some embodiments, the Activate AED Network widget takes the form of a GUI button that is displayed on an incident report screen of the CAD system. However, it should be appreciated that the widget can be implemented using a wide variety of different GUI mechanisms including pull down menus, etc., and can be displayed or accessible from any suitable UI screen.

The Activate AED Network message may take a variety of forms but generally includes at least the location (e.g., GPS coordinates, a street address or other suitable location information) of the incident. Preferably the message also can include notes that may be entered by the emergency operator. The notes may indicate further relevant details about the incident. For example, this may include further location information (e.g., the victim is located on the $3^{rd}$ floor in suite 340), details about the incident (e.g., beware of downed electrical wires), information about the victim or the victim's condition, or any other information deemed appropriate. In some embodiments, the Activate AED Message may have any number of other fields deemed relevant.

When the emergency services interface 28 receives an Activate AED Network message from a CAD system, it forwards the message to the AED network server 20 to thereby activate the AED response network. This can be accomplished by simply forwarding the received message or by creating a new message that including the relevant information.

The described architecture provides emergency operators with the ability to easily activate an AED responder network (e.g. by selecting a button on their CAD display screen) without having to be concerned with details of the responder network itself. In the illustrated embodiment all the device management, tracking, validation, selection and notifications are handled by the AED response server(s) 20 independently of the call center. It should be apparent that there will be many circumstances where a volunteer responder can arrive at the scene of a cardiac arrest incident with a defibrillator more quickly than traditional emergency medical services, which has the potential to improve incident outcomes in many circumstances.

Figure 6:
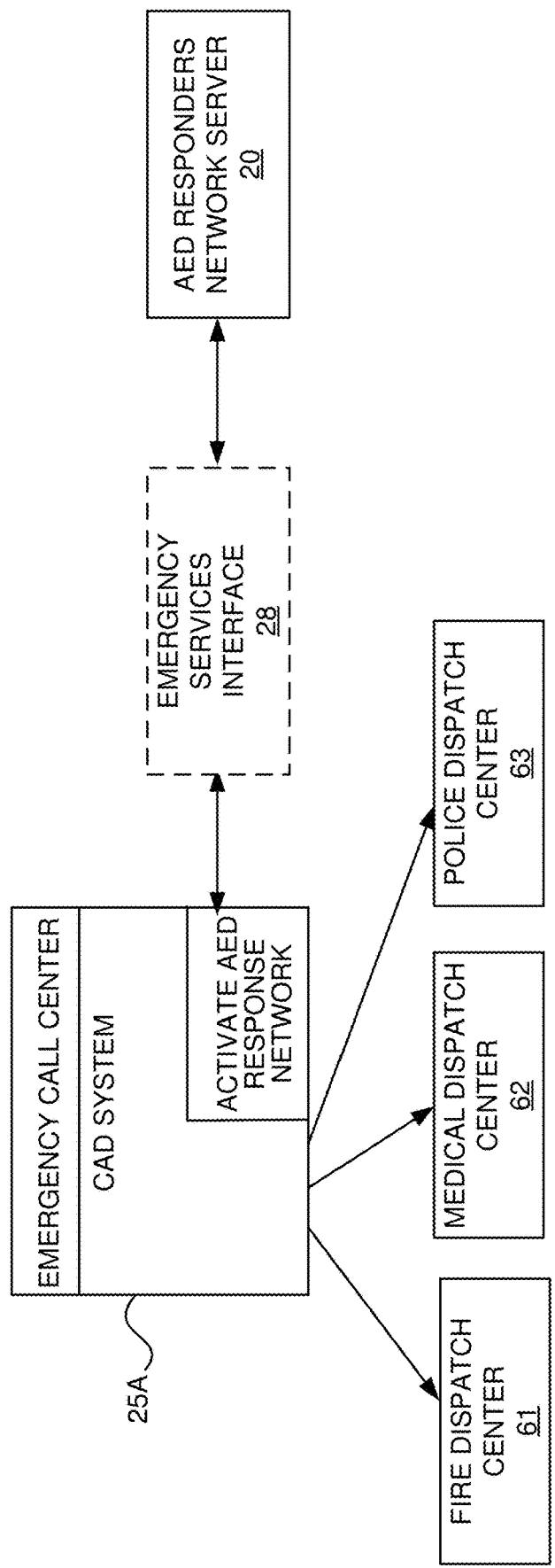
FIG. 6 is a schematic block diagram illustrating the integration of an activate AED response network widget in the context of another emergency call dispatch architecture.

Providing emergency operators with the ability to easily activate the AED responder network can have even bigger impacts in some specific situations. For example, some emergency call centers function somewhat like routing or triage centers in that they take incoming calls and determine what more specific call center the call is best routed to. One such example, illustrated in FIG. 6, is a 911 center 25A that receives incoming 911 calls, determines the type of emergency service that is best suited for handling the emergency (e.g., fire, medical, police) and then forward the call to a call center specific to that service (e.g., a fire call/dispatch center 61, a medical call/dispatch center 62, a police call/dispatch center 63, etc) but does coordinate the dispatch of emergency services itself. Although such frameworks are not too common, they do exist, and they are more often found in somewhat rural areas.

It should be apparent that such "call forwarding" can add additional delays to the response time—particularly when the receiving service specific call center (e.g. the medical call/dispatch center) happens to be busy. Such delays can be particularly problematic in cardiac arrest situations where every minute that passes before a responder arrives can adversely affect survival chances.

In such circumstances the receiving 911 center 25A can activate the AED responder network when the incident is categorized as a potential cardiac arrest incident. This can help reduce any delays associated with waiting for the call to be answered/acted on by the medical call/dispatch center 62 since volunteers in the AED responder network may be notified generally in parallel with the call forwarding which increases the possibility that a volunteer responder may arrive at the scene with an AED before traditional emergency services can arrive. Furthermore, in some specific instances, an alternative emergency service (e.g. a fire department with EMT services) may elect to participate in the AED responder network. In such circumstances, the alternative emergency service could actually receive notification of a nearby emergency cardiac arrest incident sooner through the AED responder network than they would through the ordinary dispatch protocol.

The emergency services interface 28 can also be used to facilitate transferring information to emergency services from an AED or from a user app 35 using IP communication protocols. For example, either a defibrillator app/user interface or a user app 35 can include a mechanism for contacting an emergency operator/dispatcher. An example of such a mechanism is Contact Emergency Services button 345 shown in FIG. 3E. As previously discussed, the AED may have a secure and validated connection with the AED response network server 20. When a user selects the contact Emergency Services button, a Contact Emergency Services message is sent to the AED response network server 20. The message may include the devices location, or the location may be added by the server since the server tracks the AED's location. The server, in turn, sends a request to contact emergency services to the emergency services interface 28 which, among other things is designed to identify the correct emergency call center and forward the request to the appropriate call center.

Incident data can be transferred from an AED to an emergency call center for forwarding to emergency medical personnel in substantially the same manner. As will be appreciated by those familiar with the art, during emergency use of a defibrillator, the defibrillator collects a variety of incident related information that may be useful to responding emergency medical personnel. Relevant defibrillator information can include information such as the number of shocks delivered (if any); the characteristics of such shocks (e.g., the voltage applied, the waveform applied, etc.); the timing of such shocks; the patient's measure ECGs (both before and after the delivery of a shock), etc. Although such information may be useful to medical personnel, as a practical matter it can be very difficult to convey such information to the medical personnel. One obstacle is that most AEDs don't have a mechanism for electronically sending incident information in real time during or after an incident. Even if an AED has the ability to send incident data to an AED network server, the server typically wouldn't have visibility as to what EMT team is responding to an incident and/or what medical facility (e.g. hospital) the patient may be taken to.

In contrast, in many circumstances, a call center will have a mechanism in place to deliver data or electronic information to both responding emergency personnel and/or to medical facilities to which a patient may be directed. Furthermore, emergency services interfaces such as RapidSOS are designed to deliver device data to the appropriate call center. Therefore, the AED response network server 20, the emergency services interface 28 and the appropriate call center can together form an effective intermediary for delivering defibrillator incident data to appropriate medical personnel. Such information can be delivered in real time during an incident and/or shortly after the AED has been used.

Figure 7:
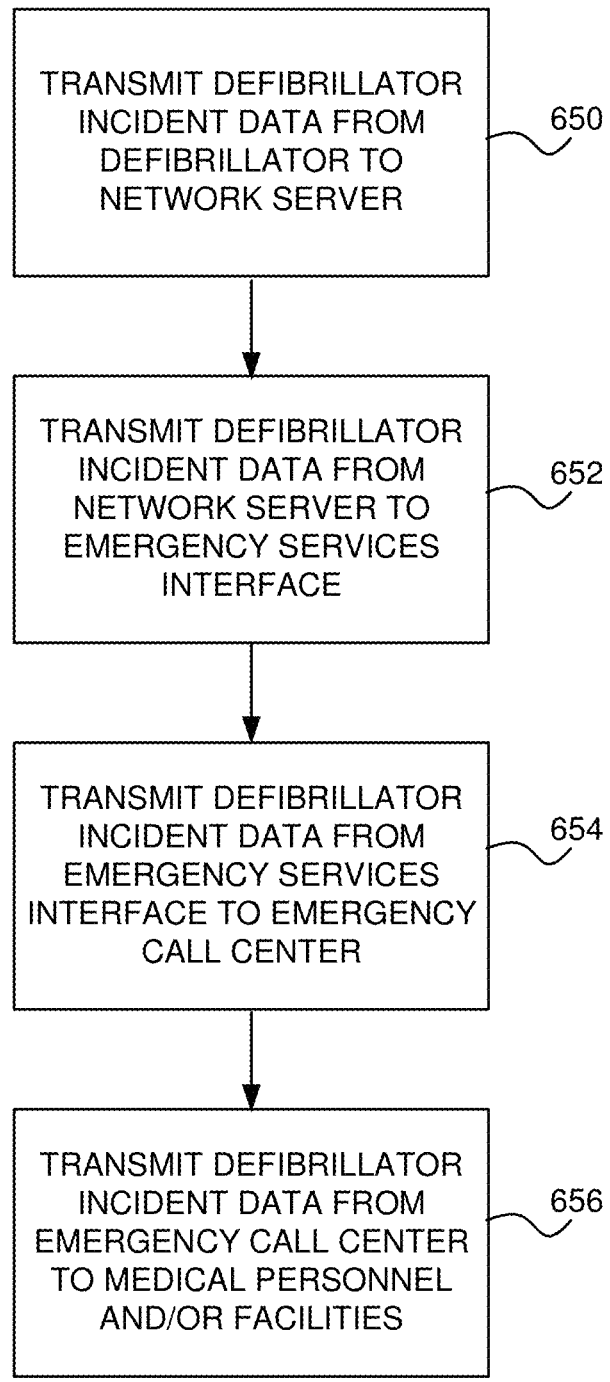
FIG. 7 is a flow chart illustrating a method of transferring incident data from a defibrillator to medical personnel and/or facilities via a defibrillator network server, and emergency services interface and an emergency call center.

FIG. 7 is a flow chart that illustrates the flow of information from a defibrillator to medical personnel and/or facilities via the network server 20, emergency services interface 28, and call center 25. As seen therein, the defibrillator transfers the relevant incident data to the network server 20 (block 650). The network server then forwards the incident data to the emergency services interface 28 (block 652). The emergency services interface, in turn, forwards the incident data to the appropriate call center (block 654). Finally, the call center forwards the incident data to the appropriate medical personnel and/or medical facilities (block 656).

Using the AED network server and emergency services interface as intermediaries in communications between the AED and emergency services has several advantages both in implementation ease and overall security. The security is enhanced because the AEDs are known an authenticated by the AED response network server 20. The AED response network server is known and trusted by the emergency services interface 28. The emergency services interface is known and trusted by the emergency call centers 25. From the perspective of the call center, any communications received over an IP connection from an AED are received from a trusted source (the emergency services interface), which can be white listed. Similarly, from the perspective of the emergency services interface 28, all data received over an IP connection from an AED are received from a trusted source (the AED response network server 20, which again can be white listed). In contrast, allowing call centers to accept connections from AEDs without going through the AED response network server would introduce a significant security risk to the call centers.

The described approach is also particularly easy to implement because the emergency services interface 28 is already a trusted data provider for many call centers, which significantly simplifies the AED response network/call center integration process.

It is noted that the described usage of the emergency services interface is believed to be quite different than emergency services interfaces that are presently commercially available. Initially, the inventors are unaware of any existing emergency services interfaces that connect an AED response network to various emergency call center CAD systems as described herein.

Further, some call centers are configured to send data (e.g., an electronic incident record) to EMS providers 27. However, the inventors are unaware of any existing emergency services interfaces that facilitate transferring incident information (e.g., the location of an incident) from a call center to a remote device (or a remote network of devices) that is not a part of the EMS network. Rather, in traditional systems incident data from remote devices 29 is only transmitted to EMS providers 27. In contrast, as described above, in the architecture illustrated in FIG. 1B, the call center 25 can send a message to the AED responder network via the emergency services interface 28.

Other Features

Although only a few embodiments of the invention have been described in detail, it should be appreciated that the invention may be implemented in many other forms without departing from the spirit or scope of the invention. For example, the drawings show a variety of specific screen shots from a user interface suitable for implementing selective features. However, it should be appreciated that the specific layout, text and graphics displayed may be widely varied based on the design needs and preferences for any particular implementation. In many circumstances GUI buttons or other GUI specific constructs are shown as the user interface mechanism for inputting information or selecting specific features. It should be apparent that the specific GUI constructs used to implement the described functionality may be widely varied and in some embodiments, some of the transitions and/or updates may be implemented automatically based on detected or received information such as the location of the responder or responding AED, the arrival of other responders, etc.

In the discussions above, there are a number of alerts and messages that are delivered to or from a volunteer responder, a connected AED, an incident bystander utilizing and AED app, etc. Such alerts and/or messages may be transmitted via any of a variety of different messaging technologies, including SMS text messages, other text or voice messaging protocols, multimedia messaging protocols (e.g., MMS), instant messaging or iMessage technologies, IP protocols (e.g., TCP/IP) and communications technologies built thereon such as e-mail, etc., and/or using any other suitable communications protocol.

Communications between the AED response network server(s) and emergency services servers or emergency response networks can also be made using any suitable communications protocol.

Much of the discussion above refers to communications between an AED and an AED network server. Some AEDs will have an integrated communications unit so that communications can be made directly with the AED. However in many other applications, the AED itself will not have a communications unit that is suitable for communicating with the AED network sever. Rather, a separate interface unit or communications unit may be provided that has such abilities. In some circumstances, the interface unit may be a very separate unit that is physically attached to a fully functional AED such that it can be (and is intended to be) carried together with the AED as a single unit even though it is architected as a modular system. In such circumstances, the AED (which might be considered a base defibrillator unit) may be a fully functional defibrillator that is capable of (and/or designed to) operate independently with or without the presence of the interface unit. In such circumstances the described communications may be with the independent interface unit or communication unit rather than the base defibrillator unit itself. A good example of such a modular system is described in the incorporated U.S. patent application Ser. No. 16/145,657. However, for the purposes of this disclosure and claims, communications with such systems is contemplated to be within the scope of the described communications with an AED unless the context precludes such interpretation.

In other applications, an interface or communications unit may be part of a dock, cabinet or other structure that an AED is stored in/on, but would not be taken together with the AED to the scene of an incident. In still other embodiments, the interface or communications unit may be a separate stand alone device intended to monitor and AED (see, e.g., U.S. Pat. No. 9,035,787), receive communications from an AED, be placed near and AED, or carried in a bag (or other carrier) with and AED. Many of the described responder network communications and functionality can be accomplished in these types of systems as well, although the ability to communicate in such systems would presumably be lost when the AED is removed from its storage location. However, such systems would still be able to communicate the location and status of the AED when the AED is present at its storage location and can generate the described nearby incident alerts. Thus, again, for the purposes of this disclosure and claims, communications with such systems is contemplated to be within the scope of the described communications with an AED unless the context precludes such interpretation.

Several of the workflows described above were described at least in part through the use of flow charts which suggest a particular order of steps. In some circumstances the order of events may be important as suggested by the context. However, in others various steps may be reordered or eliminated and other steps may be added without departing from the spirit and scope of the invention.

The inventions have been described primarily in the context of a defibrillator responder network of defibrillators and volunteers willing to respond to cardiac arrest incidents. However, it should be appreciated that a similar approaches and systems can be used in conjunction with responder networks involving other types of medical incidents, treatments and/or devices. For example, there are a number of situations in which quickly delivering a particular publically available medication to a patient can have a significant positive impact on the patient's outcome. One specific example is that an epinephrine injection is often recommended for a patient suffering from a severe allergic reaction (anaphylaxis). Similarly, some public health organizations recommend public administration of Naloxone (or other similar medications) to patients that have suffered an opioid overdose. In both of these situations, the patient or bystanders around the patient may not have immediate access to the required medication, but since these are relatively widely distributed medications, others nearby may have such medications on hand. The described responder network approaches can be used to facilitate notifying nearby volunteer responders and/or connected devices (as for example a connected first aid kit or a connected EpiPen) of the nearby incident in the same manner described above with respect to the defibrillator responder network. Similarly, the described approaches can also be used in non-medical related responder networks.

In another example, in certain regions poisonous bites (e.g., snake bites, spider bites, etc.) are of concern and quickly administering an anti-venom can significantly increase survival chances. In such regions, the responder network can be used to inform nearby volunteer responders and/or connected devices of the need for the anti-venom or antidote. Of course, there are a wide variety of other situations where there may be a need for a medical instrument, a component of a first aid kit or a medication that at least some volunteer responders may have ready access to and an appropriate responder network would be advantageous. When devices are involved, the device itself (e.g. a first aid kit, an EpiPen or other medical instrument) is connected then such devices can be integrated in the same manner as the described defibrillators. Alternatively, the connected device may be a more generic item such as a first aid kit, an anti-venom kit, a medical supply kit, a safety kit etc. that contains or potentially contains the required items. It should be apparent that the described techniques can be used in such circumstances as well.

In most of the description above, the responder network is described as sending nearby incident notifications to volunteer responders and/or AEDs. It should be appreciated that there are a wide variety of different devices to which nearby incident notifications can be sent. For example, many homes now have virtual assistants and nearby incidents messages can be sent to such systems. Examples of such a system is described in U.S. Provisional Patent Application No. 62/938,456 which is incorporated herein by reference. Some neighborhoods also have local responder networks. Notifications can be sent from the responder network server (20) to such systems for distribution to their respective members, or servers in such systems may serve as the responder network server.

In many of the embodiments described above, a map is rendered on a screen associated with the AED to help a responder navigate towards a given destination (e.g., the scene of the incident; to a particular AED; to the location to which the AED should be returned after use, etc.). In some embodiments audio or textual directions may be provided in addition to, or in place of displaying a map. In some embodiments, audible instructions may be step-by-step (turn-by-turn) instructions that are based on the user's then current location (e.g., proceed west on Fulton Street for 100 meters and turn right on $9^{th}$ Avenue. Thereafter, when the responder has reached the instructed location, the next instruction is articulated—e.g., proceed north on $9^{th}$ Avenue to 758 $9^{th}$ Avenue, the $5^{th}$ house on the right). The audible instructions may be rendered via a speaker that is part of the AED system (e.g., a speaker on an AED itself, a speaker on an interface unit attached to the AED, or on any other component associated with a portable AED system). Alternatively or additionally, step-by-step textual (written) directions may be displayed on a display screen associated with the AED system and may be updated in a generally similar manner.

Figures 5B, 5C:
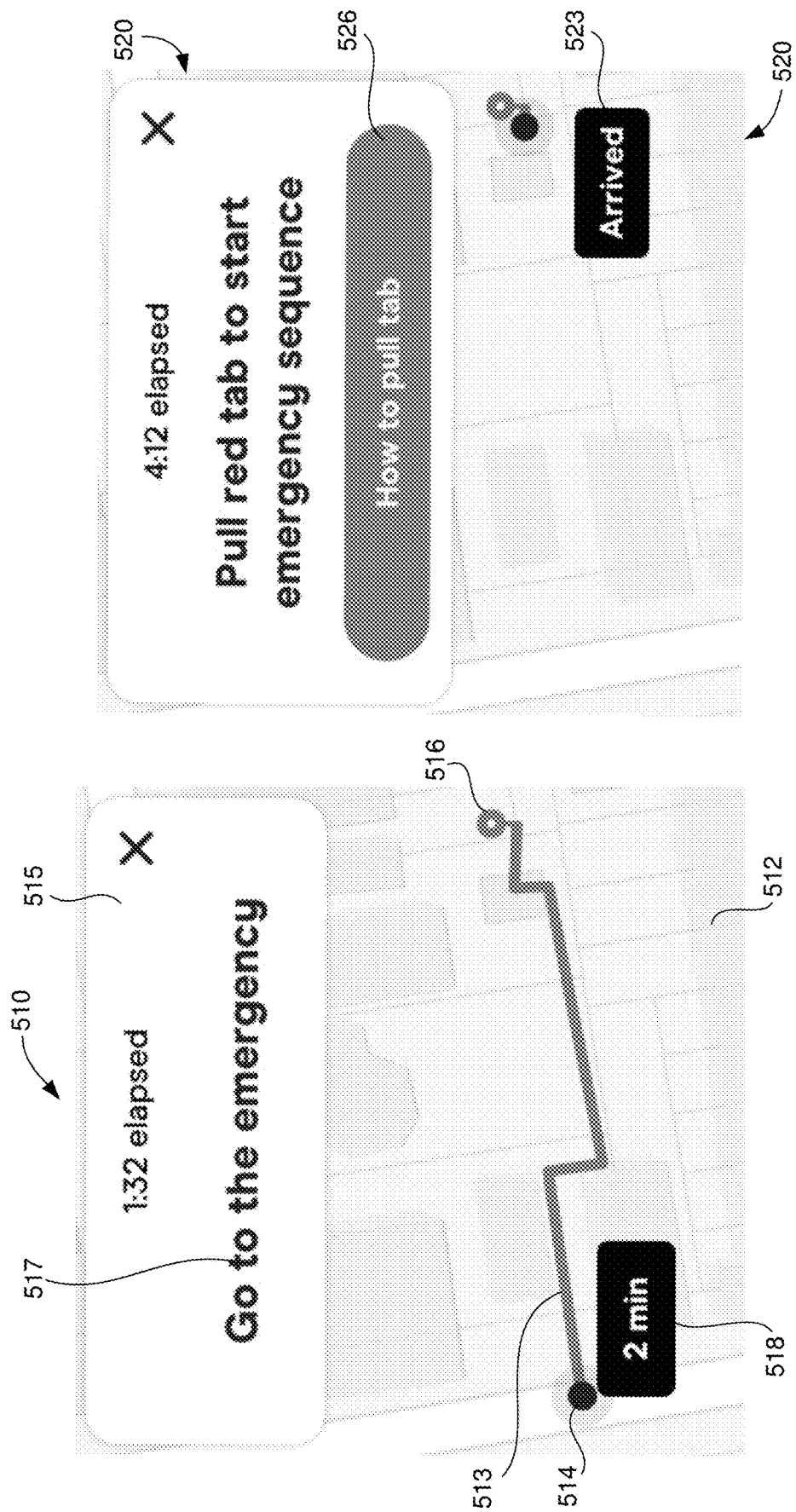
Figure 5E:
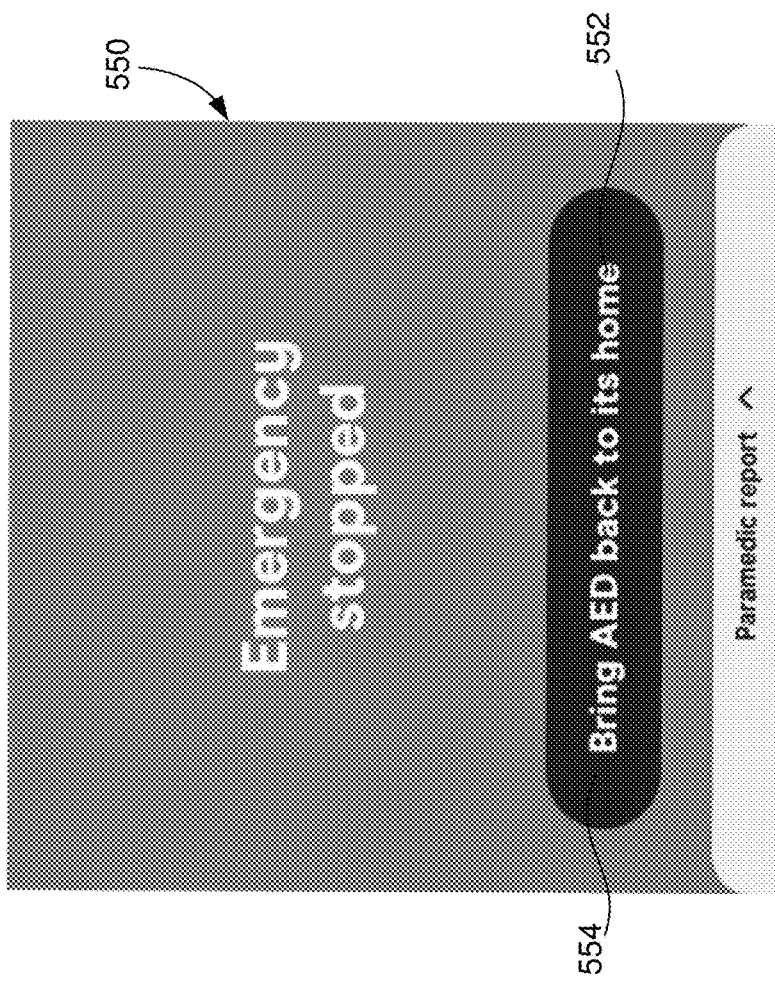
Figure 5D:
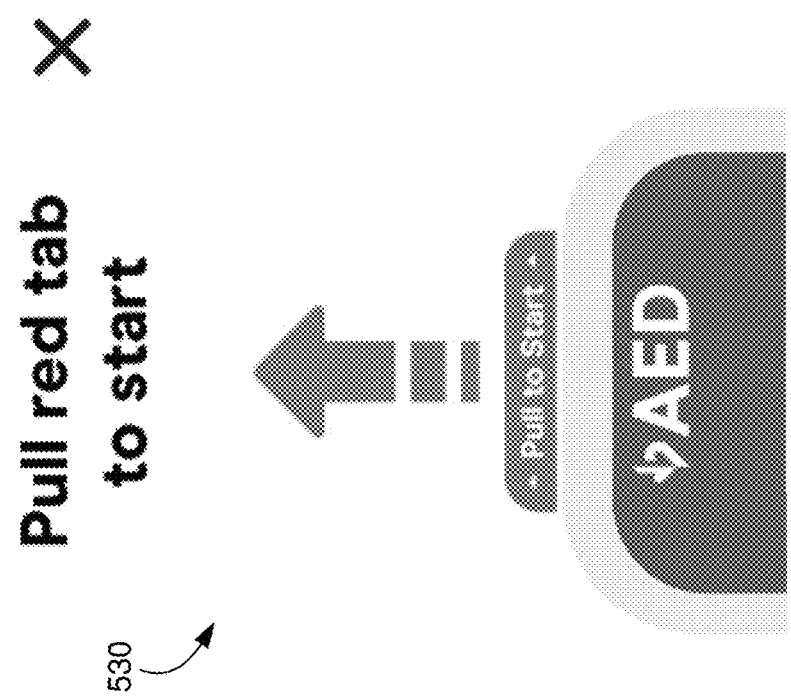
Figure 5G:
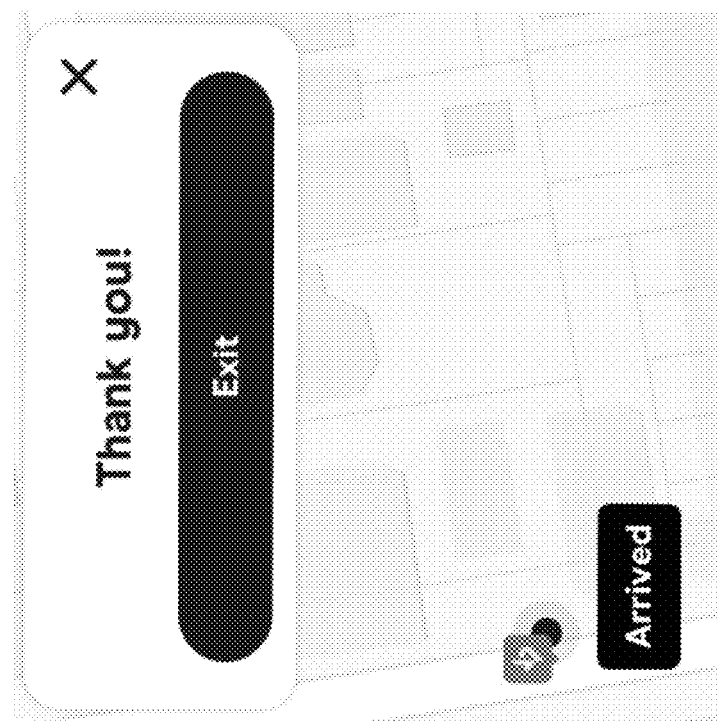
Figure 5F:
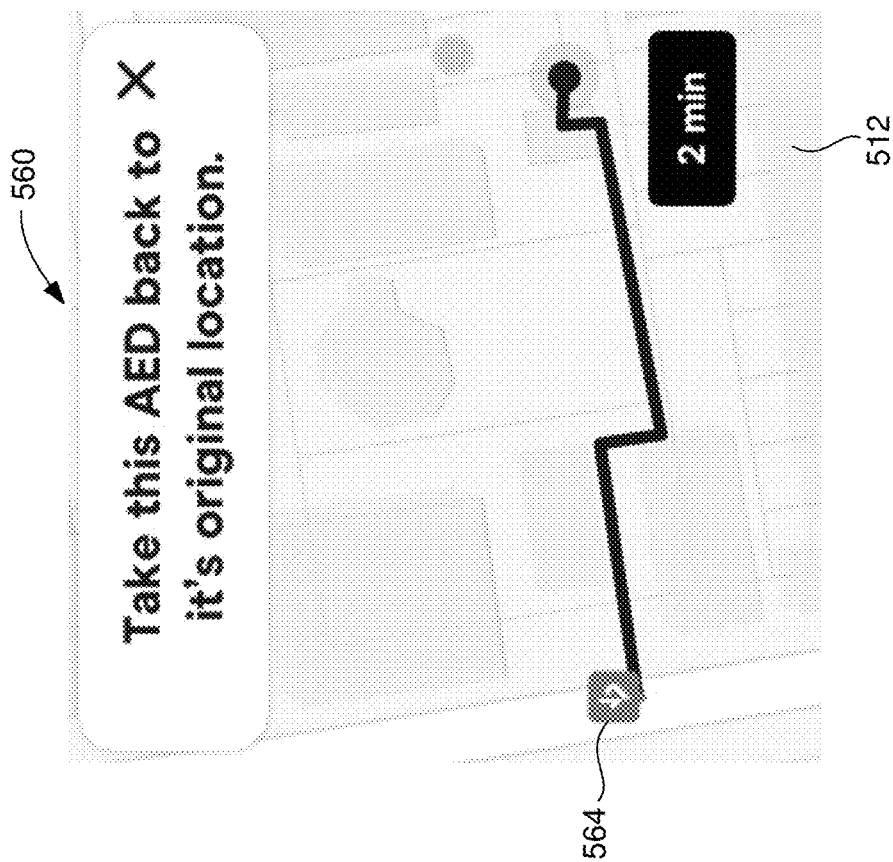
Figure 5H:
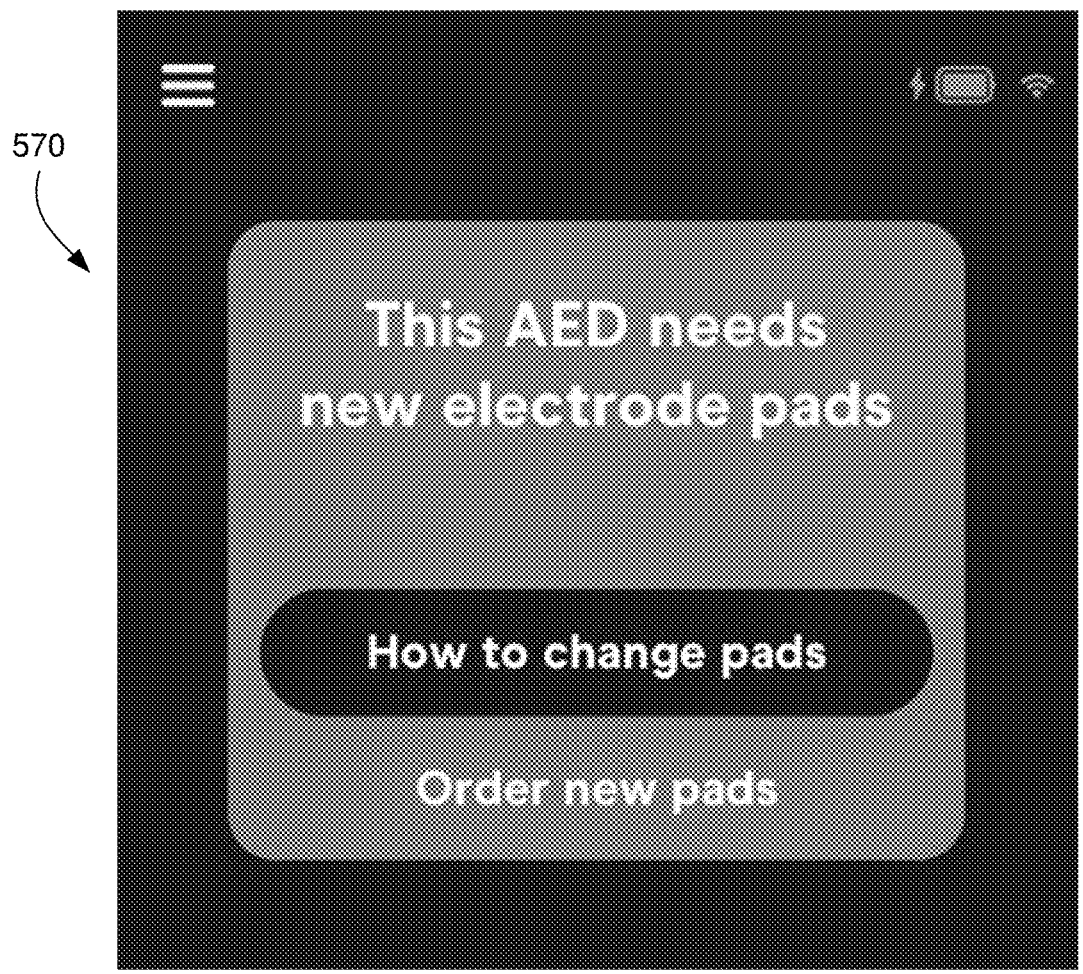

In still other embodiments, a travel path may be shown on the map to guide the responder to the desired location as shown, for example, in FIGS. 4D and 5B-5C. Preferably any such directions (audible, written, travel path or otherwise) will be updated periodically to emphasize the direction(s) from the then current location. In the case of a travel path, this may be readily accomplished by showing the current location of the AED on the screen as seen if FIGS. 4D and 5B-5C. The directions can be provided by a directions module (not shown). The directions module may execute on the responder network server that communicates with the AED system over a wireless network, or it may execute at the AED system itself. In still other embodiments, a $3^{rd}$ party direction module may be used. In some such embodiments, the responder network server may serve as an intermediary that forwards messages back and forth between the AED system and the directions module (e.g., forwarding the AED's current location to the directions module and forwarding specific direction instruction from the directions module to the AED system).

Therefore, the present embodiments should be considered illustrative and not restrictive and the invention is not to be limited to the details given herein, but may be modified within the scope and equivalents of the appended claims.

What is claimed is:

1. An automated external defibrillator (AED) system that includes an AED, a display screen and a communications unit, the AED system being configured to:
   receive an incident message that indicates a location of a potential cardiac arrest incident for which the AED may be helpful;
   in response to the reception of the incident message, (i) generate a nearby incident alert that indicates that there is the potential cardiac arrest incident nearby for which the AED system may be helpful, and (ii) render an accept incident GUI element on the display screen that a responder can interact with to accept the incident thereby indicating that the responder is willing to take the AED system to a location of the potential cardiac arrest incident, wherein the nearby incident alert includes at least one of (iii) a visual message displayed on the display screen, and (iv) an audible message;
   receive via the accept incident GUI element, the responder's acceptance of the incident indicating a willingness to help by bringing the AED to the location of the potential cardiac arrest incident;
   convey an indication of the responder's acceptance of the incident to a remotely located server; and
   render an indication of a location of the potential cardiac arrest incident, wherein the indication of the location of the potential cardiac arrest incident includes at least one of a map that shows the location of the potential cardiac arrest incident, directions to the location of the potential cardiac arrest incident, an address of the potential cardiac arrest incident, or geographic coordinates of the potential cardiac arrest incident, whereby the responder may utilize the rendered location indication to navigate to the location of the potential cardiac arrest incident, and whereby a bystander that hears or sees the nearby incident alert is encouraged to take the AED system to the location of the potential cardiac arrest incident regardless of whether the bystander is a registered responder and regardless of whether the bystander is a trained emergency responder.

2. An AED system as recited in claim 1, wherein the rendered indication of the location of the potential cardiac arrest incident is or includes the map that shows the location of the potential cardiac arrest incident, the AED system being configured to display the map that shows the location of the potential cardiac arrest incident on the display screen, whereby the responder may utilize the map displayed on the display screen to navigate to the location of the potential cardiac arrest incident.

3. An AED system as recited in claim 2 wherein the indication of the location of the potential cardiac arrest incident further includes a textual rendering of the address of the potential cardiac arrest incident.

4. An AED system as recited in claim 3 further configured to show a current location of the AED on the map and to update the current location displayed on the map as the responder navigates to the location of the potential cardiac arrest incident.

5. An AED system as recited in claim 1, wherein one of:
   the display screen and the communication unit are both components of the AED; or
   the AED system is a portable modular defibrillator system that includes a base defibrillator unit that serves as the AED and an interface unit that is mounted on the base defibrillator unit to provide the portable modular defibrillator system, wherein the communication unit and the display screen are part of the interface unit.

6. An AED system as recited in claim 1 further configured to:
   display an arrived GUI widget on the display screen, the arrived GUI widget being configured to receive a user input indicating that the AED system has arrived at the location of the potential cardiac arrest incident; and
   send an arrived at the incident location notification to the server indicting that the AED system has arrived at the location of the potential cardiac arrest incident in response to receipt of the user input indicating that the AED system has arrived at the location of the potential cardiac arrest incident.

7. An AED system as recited in claim 1 further configured to automatically transition to displaying an AED operating instruction when the AED is determined to have arrived at the location of the potential cardiac arrest incident.

8. An AED system as recited in claim 1 further configured to transition to displaying an AED operating instruction, in response to a user input indicative that the AED has arrived at the location of the potential cardiac arrest incident.

9. An AED system as recited in claim 1 further configured to support messaging between the responder and a telecommunicator at a public safety answering point (PSAP).

10. An automated external defibrillator (AED) system comprising an AED capable of delivering a defibrillation shock to a patient experiencing cardiac arrest, a speaker, a display screen and a communications unit, the AED system being configured to:
    receive an incident message that indicates a location of a potential cardiac arrest incident for which the AED may be helpful;
    in response to the reception of the incident message, (i) generate a nearby incident alert that indicates that there is the potential cardiac arrest incident nearby for which the AED system may be helpful, and (ii) render an accept incident GUI element on the display screen that a responder can interact with to accept the incident thereby indicating that the responder is willing to take the AED system to a location of the potential cardiac arrest incident, wherein the nearby incident alert includes at least one of (iii) a visual message displayed on the display screen, and (iv) an audible message;
    receive via the accept incident GUI element, the responder's acceptance of the incident indicating a willingness to help by bringing the AED to the location of the potential cardiac arrest incident;
    convey an indication of the responder's acceptance of the incident to a remotely located server; and
    render a map on the display screen, wherein the map shows the location of the potential cardiac arrest incident;
    update the map displayed on the display screen as the responder navigates with the AED towards the location of the potential cardiac arrest incident, wherein the update of the map is or includes updating a current location of the AED displayed on the map as the responder navigates with the AED towards the location of the potential cardiac arrest incident; and convey an arrived notification to the remote server indicating that the AED system has arrived at the location of the potential cardiac arrest incident when the AED system is determined to have arrived at the location of the potential cardiac arrest incident.

11. An AED system as recited in claim 10 further configured to automatically transition to displaying an AED use instruction when the AED is determined to have arrived at the location of the potential cardiac arrest incident.

12. An AED system as recited in claim 10 further configured to transition to displaying an AED operating instruction, in response to a user input indicating that the AED has arrived at the location of the potential cardiac arrest incident.

13. An AED system as recited in claim 10 further configured to show the directions to the location of the potential cardiac arrest incident on the display screen, the directions to the location of the potential cardiac arrest incident being from the current location of the AED.

14. An AED system as recited in claim 13 wherein the directions include textual directions displayed on the display screen, whereby the responder may utilize the textual directions displayed on the display screen to navigate to the location of the potential cardiac arrest incident.

15. An AED system as recited in claim 10 wherein the AED system is further configured to provide audio directions to the location of the potential cardiac arrest incident via the speaker, whereby the responder may be directed to the location of the potential cardiac arrest incident by the audio directions.

16. An AED system as recited in claim 1 further configured to support electronic messaging between the responder and a witness present at the location of the potential cardiac arrest incident.

17. An AED system as recited in claim 10, wherein the AED system is a portable modular defibrillator system that includes a base defibrillator unit that serves as the AED and an interface unit that is mounted on and attached to the base defibrillator unit to provide the portable modular defibrillator system, wherein the communication unit and the display screen are part of the interface unit.

18. An AED system as recited in claim 10, wherein the display screen and the communication unit are both components of the AED.

19. An AED system as recited in claim 10, further configured to display at least one of:
    a timer that indicates an amount of time that has elapsed since a call for help was made or a potential cardiac arrest incident was declared; and
    an estimate of how long it will take to arrive at the location of the potential cardiac arrest incident.

20. An AED system as recited in claim 1 wherein the communications unit is a wireless communications unit, and the AED system further comprises a messaging interface that facilitates the rendering of notes, the AED system being further configured to:
    receive notes regarding the potential cardiac arrest incident from a remotely located source via the communications unit, the notes being distinct from the indication of the location of the potential cardiac arrest incident; and
    render the notes regarding the potential cardiac arrest incident.

21. An AED system as recited in claim 20, wherein the outputted indication of the location of the potential cardiac arrest incident and the notes are both at least partially rendered on the display screen.

22. An AED system as recited in claim 20 wherein the notes are dispatcher notes entered by a public safety answering point (PSAP) operator.

23. An AED system as recited in claim 10 further configured to support messaging between the responder and a telecommunicator at a public safety answering point (PSAP).

24. An AED system as recited in claim 10 wherein the AED system is determined to have arrived at the location of the potential cardiac arrest incident based at least in part on at least one of:
    (v) a user input to the AED system indicating that the AED system has arrived at the location of the potential cardiac arrest incident, and
    (vi) an automatic determination that the AED system has arrived at the location of the potential cardiac arrest incident.

\* \* \* \* \*